(12) United States Patent
Oda

(10) Patent No.: US 9,377,537 B2
(45) Date of Patent: Jun. 28, 2016

(54) RADIOGRAPHIC IMAGE CAPTURE DEVICE, METHOD AND PROGRAM STORAGE MEDIUM

(71) Applicant: FUJIFILM Corporation, Tokyo (JP)

(72) Inventor: Yasufumi Oda, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 14/725,644

(22) Filed: May 29, 2015

(65) Prior Publication Data

US 2015/0260852 A1 Sep. 17, 2015

Related U.S. Application Data

(63) Continuation of application No. 13/711,514, filed on Dec. 11, 2012, now Pat. No. 9,063,239.

(30) Foreign Application Priority Data

Jan. 27, 2012 (JP) ................. 2012-015944

(51) Int. Cl.
*G01T 1/24* (2006.01)
*H01L 27/00* (2006.01)
*G01T 1/17* (2006.01)
*A61B 6/00* (2006.01)
*H04N 5/32* (2006.01)
*H04N 5/232* (2006.01)
*H04N 5/361* (2011.01)

(52) U.S. Cl.
CPC . *G01T 1/17* (2013.01); *A61B 6/548* (2013.01); *G01T 1/24* (2013.01); *H04N 5/23206* (2013.01); *H04N 5/32* (2013.01); *H04N 5/361* (2013.01)

(58) Field of Classification Search
CPC ............ G01T 1/24; G01T 1/17; A61B 6/548; H04N 5/32; H04N 5/23206; H04N 5/361
USPC ...................................... 250/370.08
See application file for complete search history.

(56) References Cited

U.S. PATENT DOCUMENTS 4,719,343 A * 1/1988 Tressler, III ............... 250/208.6
7,768,002 B2 8/2010 Kitamura et al.
7,829,860 B2 * 11/2010 Nygard et al. ........... 250/370.09
(Continued)

FOREIGN PATENT DOCUMENTS

JP 2011-177356 A 9/2011

OTHER PUBLICATIONS

United States Office Action dated Nov. 26, 2014 in U.S. Appl. No. 13/711,514.
(Continued)

*Primary Examiner* — David Porta
*Assistant Examiner* — Abra Fein
(74) *Attorney, Agent, or Firm* — McGinn IP Law Group PLLC

(57) ABSTRACT

A radiographic image capture device includes a radiation detector and a determination section. The radiation detector includes a first sensor for radiographic image capture and a second sensor for radiation detection. The determination section determines whether or not radiation has been detected by the radiation detector based on a ratio of a first value obtained by the first sensor to a second value obtained by the second sensor.

18 Claims, 18 Drawing Sheets

(56) References Cited

U.S. PATENT DOCUMENTS

2002/0153488 A1   10/2002   Utukuri et al.
2002/0153491 A1   10/2002   Sugawara et al.
2004/0113046 A1*  6/2004   Gorder et al. .............. 250/208.1
2005/0274991 A1   12/2005   Ishii et al.
2007/0210255 A1    9/2007   Bjorkholm
2009/0129659 A1*  5/2009   Deutschmann ............... 382/132
2011/0180717 A1*  7/2011   Okada ..................... 250/370.08

OTHER PUBLICATIONS

United States Notice of Allowance dated Feb. 19, 2015 in U.S. Appl. No. 13/711,514.
United States Office Action dated Jun. 4, 2014 in U.S. Appl. No. 13/711,514.

* cited by examiner

FIG.17

INITIAL DATA INPUT SCREEN

PLEASE INPUT SUBJECT NAME, IMAGING TARGET SITE, IMAGE CAPTURE POSTURE AND EXPOSURE CONDITIONS

NAME:
IMAGING TARGET SITE:
IMAGE CAPTURE POSTURE
EXPOSURE CONDITIONS
    VALVE VOLTAGE
    VALVE CURRENT

COMPLETE

RADIOGRAPHIC IMAGE CAPTURE DEVICE, METHOD AND PROGRAM STORAGE MEDIUM

RELATED APPLICATIONS

The present application is a Continuation application of U.S. patent application Ser. No. 13/711,514, filed on Dec. 11, 2012, which is based on and claims priority from Japanese Application No. 2012-015944, filed on Jan. 27, 2012, the entire contents of which is incorporated herein by reference.

BACKGROUND OF THE INVENTION

1. Field of the Invention

The present invention relates to a radiographic image capture device, method and program storage medium, and in particular to a radiographic image capture device, method and program storage medium that captures a radiographic image expressing radiation passed through a subject.

2. Description of the Related Art

Recently, radiation detectors such as Flat Panel Detectors (FPDs) are being implemented in which a radiation sensitive layer is disposed on a Thin Film Transistor (TFT) active matrix substrate and with which radiation can be converted directly into digital data. Radiographic image capture devices that employ such radiation detectors and can capture radiographic images expressing irradiated radiation are also being implemented. Radiation conversion methods used by radiation detectors employed in such radiographic image capture devices include indirect conversion methods, in which radiation is first converted into light with a scintillator and then the converted light is converted into electric charge with a semiconductor layer such as a photodiode, or direct conversion methods in which radiation is converted into electric charge with a semiconductor layer such as amorphous selenium. There are various materials that may be used in the semiconductor layer for each method.

In such radiographic image capture devices, if the radiographic image capture device itself can detect states such as initiation of radiation irradiation, termination of radiation irradiation, and an irradiation dose (amount) of radiation, it becomes unnecessary to connect an image capture control device (referred to as a console) that performs overall control of the radiographic image capture device and the radiation source to the radiation source. Such a configuration is preferable from the perspective of simplifying the system configuration and simplifying control by the image capture control device.

A radiation detection method utilizing a histogram is disclosed in Japanese Patent Application Laid-Open (JP-A) No. 2011-177356 as technology related to such types of radiographic image capture devices capable of detecting the irradiation state of radiation. In this technology, initiation of radiation irradiation is determined based on a frequency distribution of difference data obtained by voting difference data between data of adjacent radiation detection elements on a detection section onto a single histogram for each frame.

However, in the technology disclosed in JP-A No. 2011-177356, since radiation is detected by employing difference data between data for adjacent radiation detection elements, the smaller the irradiation amount of radiation, the smaller the value of the difference data. In this technology the detection precision of radiation accordingly decreases as the irradiation amount of radiation is smaller.

SUMMARY

In consideration of the above circumstances the present invention provides a radiographic image capture device, method and program storage medium capable of detecting radiation at high precision irrespective of the irradiation amount of radiation.

A first aspect of the present invention is a radiographic image capture device including: a radiation detector including a first sensor for radiographic image capture and a second sensor for radiation detection; and a determination section that determines whether or not radiation has been detected by the radiation detector based on a ratio of a first value obtained by the first sensor to a second value obtained by the second sensor.

In the radiographic image capture device of the present aspect, using the radiation detector with the first sensor for radiographic image capture and the second sensor for radiation detection, radiographic image capture is performed based on values obtained by the first sensor and radiation is detected based on the values obtained by the second sensor.

Determination as to whether or not radiation has been detected by the radiation detector is made by the determination section based on the first value obtained by the first sensor and the second value obtained by the second sensor.

Namely, in contrast to the conventional technology that compares difference data between data of adjacent radiation detection elements (pixels), radiation detection can be performed at higher precision and irrespective of the radiation irradiation amount by employing a ratio of the second value that has been obtained by the second sensor for radiation detection to the first value that has been obtained by the first sensor for radiographic image capture in order to determine whether or not radiation has been detected by the radiation detector.

Accordingly, in the radiographic image capture device of the present aspect, radiation detection can be performed at high precision irrespective of the radiation irradiation amount.

The present aspect may be configured such that: the first sensor includes plural radiographic imaging pixels that each include a conversion portion that converts irradiated radiation into electrical charge and a switching element that is switched ON when reading electrical charge obtained by the conversion portion; the second sensor includes plural radiation detection pixels that each include a conversion portion and are enabled for direct reading of electrical charge obtained by the conversion portions; the radiation detector includes the plural radiographic imaging pixels and the plural radiation detection pixels arrayed in a matrix formation, in which an array containing only the radiographic imaging pixels and an array including at least one radiation detection pixel are included, and plural signal lines, each of which is connected to the pixels arrayed in a different one of the arrays; and the determination section uses a value representing electrical charge read from a first signal line, which is a signal line provided for the array containing only the radiographic imaging pixels, as the first value, uses a value representing electrical charge read from a second signal line, which is a signal line provided for the array including the at least one radiation detection pixels, as the second value, and determines that radiation has been detected by the radiation detection pixels if a condition of the ratio of the second value to the first value being a first threshold value or greater is satisfied, and otherwise determines that radiation has not been detected, electrical charge being read from the first signal line and the second line after switching all of the switching elements OFF. Consequently, as a result of being able to make a clear difference between the first value and the second value, more certain radiation detection can be achieved.

The present aspect may be configured such that: the radiographic image capture device further includes an offset correction section that performs offset correction on the first value and the second value to reduce the influence of electrical charge that arises from dark current occurring in the conversion portions and/or reduce the influence of switching noise that occurs when the switching elements are switched, wherein the determination section performs the determination employing the first value and the second value that have been subjected to the offset correction by the offset correction section. Consequently, radiation detection can be achieved at higher precision.

The present aspect may be configured such that: the radiographic image capture device further includes a fixed noise correction section that performs fixed noise reduction correction on the first value and the second value to reduce the influence of fixed noise that inherently occurs according to array positions of the radiographic imaging pixels and the radiation detection pixels, wherein the determination section performs the determination using the first value and the second value that have been subjected to the fixed noise reduction correction by the fixed noise correction section. Consequently, radiation detection can be achieved at higher precision.

The present aspect may be configured such that the determination section performs the determination using, as the first value, a summed value of values representing electrical charge that is successively read a predetermined number of times from the first signal line and using, as the second value, a summed value of values representing electrical charge that is successively read the predetermined number of times from the second signal line. Consequently, radiation detection can be achieved at higher precision than cases in which summation is not performed.

In particular, in the above case, the values subject to the summation may be values within a predetermined range. Consequently, radiation detection can be achieved at higher precision as a result of being able to suppress the influence of such factors as unforeseen noise.

The present aspect may be configured such that the determination section performs the determination plural times using different combinations of the first value and the second value, and determines that radiation has been detected by the radiation detection pixels if a number of combinations satisfying the condition equals a second threshold value or greater, and otherwise determines that radiation has not been detected. Consequently, radiation detection can be achieved at higher precision than in cases in which determination is performed with only a single combination.

The present aspect may be configured such that the determination section performs the determination employing the first value and the second value representing electrical charge that has been read from the first signal line and the second signal line and the first signal line and the second signal line are adjacent to each other. Consequently, radiation detection can be achieved at higher precision as a result of being able to perform determination between values obtained under substantially matched conditions such as temperature, load and extraneous noise.

The present aspect may be configured further including a controller that activates operation of the radiographic image capture device to capture a radiographic image with the radiation detector if the determination section has determined that the radiation detection pixels have detected radiation. Consequently, as a result of being able to detect radiation with higher precision, a capture of unnecessary radiographic images due to misdetection of radiation may be avoided.

The present aspect may also be configured such that the switching element of each of the radiation detection pixels is shorted across switch terminals. Consequently, the radiation detector can be configured more simply.

A second aspect of the present invention is a radiographic image capture method including: computing, for a radiation detector including a first sensor for radiographic image capture and a second sensor for radiation detection, a ratio of a first value obtained by the first sensor to a second value obtained by the second sensor; and determining whether or not radiation has been detected by the radiation detector based on the computed ratio.

Since operation of the second aspect is similar to that of the first aspect, the second aspect can similarly achieve radiation detection at high precision irrespective of the irradiation amount of radiation.

A third aspect of the present invention is a non-transitory storage medium stored with a program that causes a computer to execute radiographic image capture processing, the radiographic image capture processing including: computing, for a radiation detector including a first sensor for radiographic image capture and a second sensor for radiation detection, a ratio of a first value obtained by the first sensor to a second value obtained by the second sensor; and determining whether or not radiation has been detected based on the computed ratio.

Since operation of the third aspect is similar to that of the first aspect, the third aspect can similarly achieve radiation detection at high precision irrespective of the radiation irradiation amount.

Thus, according to the present aspects, radiation detection can be performed at high precision irrespective of the irradiation amount of radiation.

BRIEF DESCRIPTION OF THE DRAWINGS

Exemplary embodiments of the present invention will be described in detail based on the following figures, wherein:

FIG. 17 is a schematic diagram illustrating an example of an initial data input screen;

DETAILED DESCRIPTION

Hereinafter, an example of a case in which an embodiment is applied to a radiology information system, which is a system that as a whole manages information handled in a radiology department in a hospital, will be described.

Figure 1:
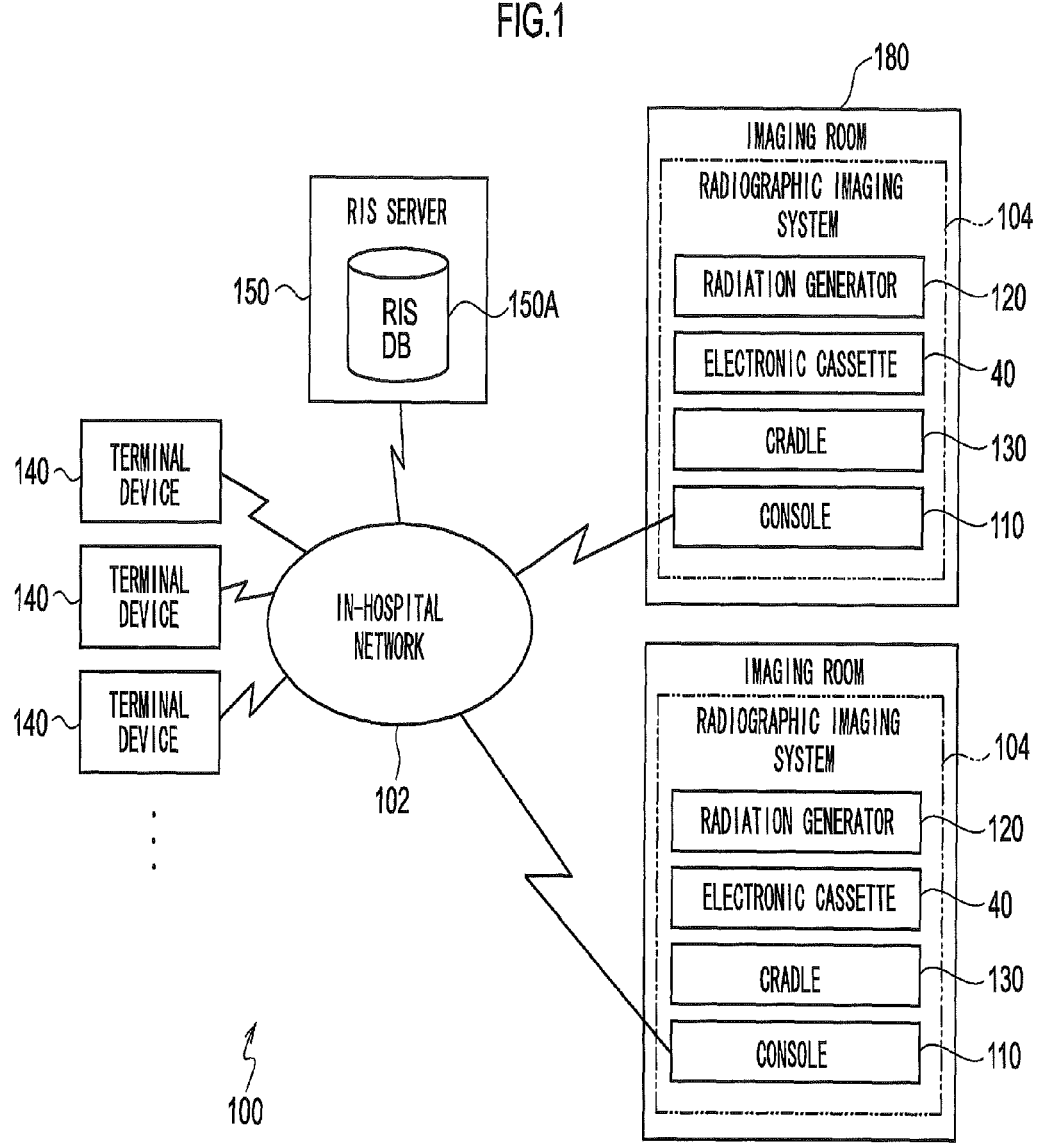
FIG. 1 is a block diagram illustrating a configuration of a radiographic image capture system according to an exemplary embodiment.

First, the configuration of a radiology information system (RIS) 100 pertaining to the present exemplary embodiment will be described with reference to FIG. 1.

The RIS 100 is a system for managing information such as medical service appointments and diagnostic records in a radiology department and configures part of a hospital information system (HIS).

The RIS 100 has plural imaging request terminal devices (terminal devices) 140, an RIS server 150, and radiographic image capture systems (the imaging system) 104. The imaging systems 104 are installed in individual radiographic imaging rooms (or operating rooms) in a hospital. The RIS 100 is configured as a result of the terminal devices 140, the RIS server 150, and the imaging systems 104 being connected to an in-hospital network 102 configured by a wired or wireless local area network (LAN). The RIS 100 configures part of the HIS disposed in the same hospital, and an HIS server (not shown in the drawings) that manages the entire HIS is also connected to the in-hospital network 102.

The terminal devices 140 are for doctors or radiologic technologists to input and browse diagnostic information and facility reservations. Radiographic imaging requests and imaging reservations are also made via the terminal devices 140. Each of the terminal devices 140 includes a personal computer having a display device, and the terminal devices 140 are made capable of intercommunicating with the RIS server 150 via the in-hospital network 102.

The RIS server 150 receives imaging requests from each of the terminal devices 140 and manages radiographic imaging schedules in the imaging systems 104. The RIS server 150 includes a database 150A.

The database 150A includes: information relating to patients (subjects), such as attribute information (names, sexes, dates of birth, ages, blood types, body weights, patient identifications (IDs), etc.), medical histories, consultation histories, radiographic images that have been captured in the past, etc.; information relating to later-described electronic cassettes 40 used in the imaging systems 104, such as identification numbers (ID information), models, sizes, sensitivities, dates of first use, numbers of times used, etc.; and environment information representing the environments in which radiographic images are captured using the electronic cassettes 40—that is, the environments in which the electronic cassettes 40 are used (e.g., radiographic imaging rooms, operating rooms, etc.).

The imaging systems 104 capture radiographic images as a result of being operated by the doctors or the radiologic technologists in response to an instruction from the RIS server 150. Each of the imaging systems 104 is equipped with a radiation generator 120 that applies a dose of radiation X (see also FIG. 7) according to exposure conditions from a radiation source 121 (see also FIG. 9) to a subject. Further, each of the imaging systems 104 is equipped with an electronic cassette 40, a cradle 130, and a console 110. The electronic cassette 40 has a built-in radiation detector 20 (see also FIG. 7) that absorbs the radiation X that has passed through an imaging target site of the subject, generates electric charges, and creates image information representing a radiographic image on the basis of the generated electric charge quantity. The cradle 130 charges a battery that is built into the electronic cassette 40. The console 110 controls the electronic cassette 40 and the radiation generator 120.

The console 110 acquires various types of information (data) stored in the database 150A from the RIS server 150, stores the data in a later-described HDD 116 (see FIG. 9), uses the data as needed to control the electronic cassette 40 and the radiation generator 120.

Figure 2:
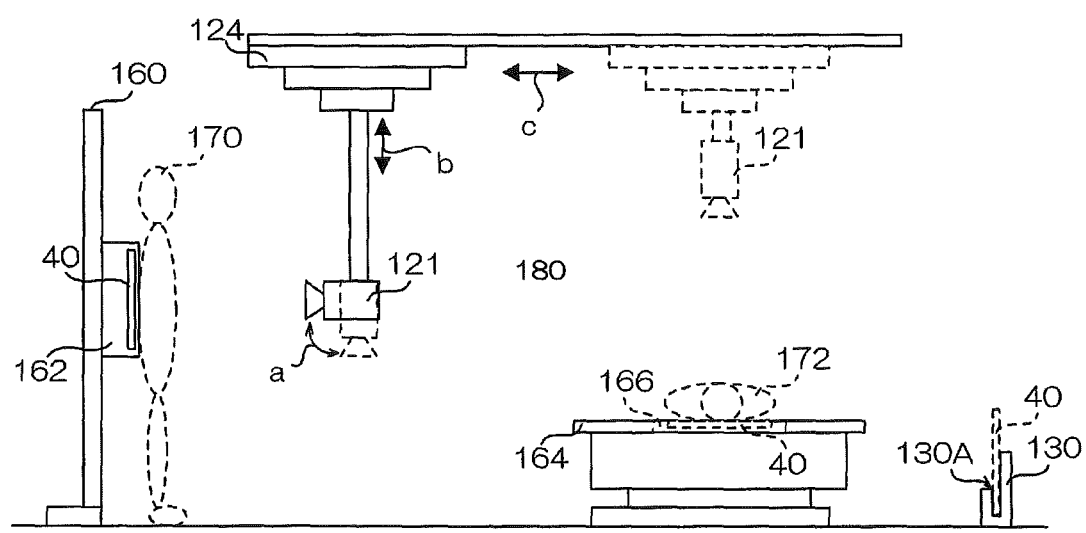
FIG. 2 is a side view illustrating an example arrangement of each device in a radiographic imaging room of the radiographic image capture system.

FIG. 2 shows an example arrangement of the devices, in a radiographic imaging room 180 of the imaging system 104 pertaining to the present exemplary embodiment.

As shown in FIG. 2, a standing position stand 160, which is used in cases of performing radiographic imaging in a standing position, and a lying position table 164, which is used in cases of performing radiographic imaging in a lying position, are installed in the radiographic imaging room 180. The space in front of the standing position stand 160 serves as a subject imaging position 170 when performing radiographic imaging in the standing position. The space above the lying position table 164 serves as a subject imaging position 172 when performing radiographic imaging in the lying position.

A holding unit 162 that holds the electronic cassette 40 is disposed in the standing position stand 160. The electronic cassette 40 is held at the holding unit 162 when capturing a radiographic image in the standing position. Similarly, a holding unit 166 that holds the electronic cassette 40 is disposed in the lying position table 164. The electronic cassette 40 is held at the holding unit 166 when capturing a radiographic image in the lying position.

Further, a supporting and moving mechanism 124 is disposed in the radiographic imaging room 180. In order to enable both radiographic imaging in the standing position and in the lying position by the radiation from the single radiation source 121, the supporting and moving mechanism 124 supports the radiation source 121 in such a way that the radiation source 121 is rotatable about a horizontal axis (the direction of arrow a in FIG. 2), is movable in the vertical direction (the direction of arrow b in FIG. 2), and is movable in the horizontal direction (the direction of arrow c in FIG. 2). The supporting and moving mechanism 124 includes a drive source that rotates the radiation source 121 about the horizontal axis, a drive source that moves the radiation source 121 in the vertical direction, and a drive source that moves the radiation source 121 in the horizontal direction (illustration of the drive sources are omitted in the drawings).

An accommodating portion 130A that can accommodate the electronic cassette 40 is formed in the cradle 130.

When the electronic cassette 40 is not in use, the electronic cassette 40 is accommodated in the accommodating portion 130A of the cradle 130, and the built-in battery of the electronic cassette 40 is charged by the cradle 130. When a radiographic image is to be captured, the electronic cassette 40 is removed from the cradle 130 by, for example, a radiologic technologist and is held in the holding unit 162 of the standing position stand 160 if the imaging posture is the standing position, or is held in the holding unit 166 of the lying position table 164 if the imaging posture is the lying position.

In the imaging system 104 pertaining to the present exemplary embodiment, various types of information (data) are transmitted and received via wireless communication between the radiation generator 120 and the console 110 and between the electronic cassette 40 and the console 110.

The electronic cassette 40 is not limited to only being employed in a state held by the holding unit 162 of the standing position stand 160 or the holding unit 166 of the lying position table 164. Due to its portability, the electronic cassette 40 may also be employed unrestrained by a holding unit, for example when imaging arm or leg regions of a subject.

Figure 3:
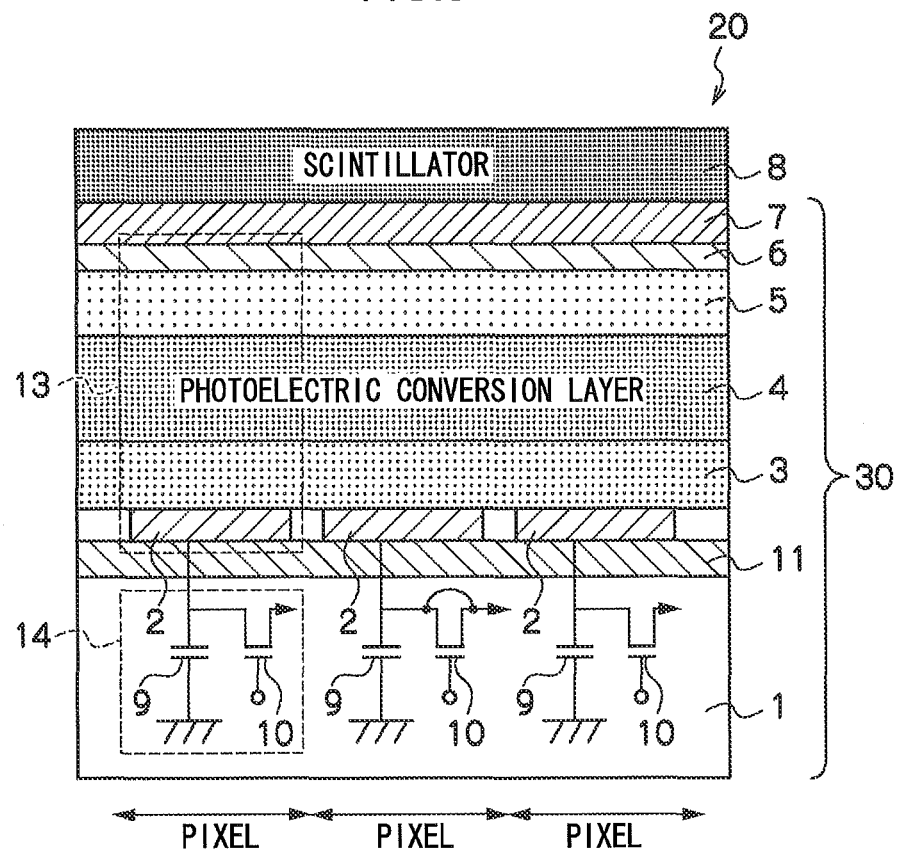
FIG. 3 is a cross-sectional diagram illustrating a schematic configuration of a portion including three pixels of a radiation detector of an exemplary embodiment.

Next, the configuration of the radiation detector 20 pertaining to the present exemplary embodiment will be described. FIG. 3 is a cross-sectional diagram schematically showing a portion including three pixels of the radiation detector 20 pertaining to the present exemplary embodiment.

As shown in FIG. 3, in the radiation detector 20 pertaining to the present exemplary embodiment, signal output portions 14, sensor portions 13, and a scintillator 8 are sequentially layered on an insulating substrate 1. Pixels are configured by the signal output portions 14 and the sensor portions 13. The pixels are arrayed on the substrate 1 and are configured such that the signal output portion 14 and the sensor portion 13 in each pixel have overlap.

The scintillator 8 is formed on the sensor portions 13 with a transparent insulating film 7 being interposed therebetween. The scintillator 8 is formed of a phosphor material that converts radiation made incident thereon from above (the opposite side of the substrate 1) or below into light and emits light. By disposing the scintillator 8, the radiation that has passed through the subject is absorbed by the scintillator 8 and light is emitted.

It is preferred that the wavelength range of the light emitted by the scintillator 8 is in the visible light range (i.e., a wavelength of 360 nm to 830 nm). It is more preferred that the wavelength range of the light that the scintillator 8 emits include the green wavelength range in order to enable monochrome imaging by the radiation detector 20.

As the phosphor used for the scintillator 8, specifically a phosphor including cesium iodide (CsI) is preferred in the case of imaging using X-rays as the radiation. Using CsI(Tl) (cesium iodide to which thallium has been added) whose emission spectrum when X-rays are applied is 400 nm to 700 nm is particularly preferred. The emission peak wavelength in the visible light range of CsI(Tl) is 565 nm.

The sensor portions 13 have an upper electrode 6, lower electrodes 2, and a photoelectric conversion layer 4 that is placed between the upper electrode 6 and the lower electrodes 2. The photoelectric conversion layer 4 is formed of an organic photoelectric conversion material that absorbs the light emitted by the scintillator 8 and generates electric charge.

It is preferred that the upper electrode 6 be formed of a conducting material that is transparent at least with respect to the emission wavelength of the scintillator 8, because it is necessary to allow the light produced by the scintillator 8 to be made incident on the photoelectric conversion layer 4. Specifically, using a transparent conducting oxide (TCO) whose transmittance with respect to visible light is high and whose resistance value is small is preferred. Although a metal thin film of Au or the like may also be used as the upper electrode 6, since its resistance value easily increases when trying to obtain a transmittance of 90% or more, TCO is more preferred. For example, ITO, IZO, AZO, FTO, $SnO_2$, $TiO_2$, $ZnO_2$, etc. may be preferably used. ITO is most preferred from the standpoints of process ease, low resistance, and transparency. The upper electrode 6 may have a single configuration common to all the pixels or may be divided per pixel.

The photoelectric conversion layer 4 includes an organic photoelectric conversion material, absorbs the light emitted from the scintillator 8, and generates an electric charge corresponding to the absorbed light. The photoelectric conversion layer 4 including the organic photoelectric conversion material has a sharp absorption spectrum in the visible range, and virtually no electromagnetic waves other than the light emitted by the scintillator 8 are absorbed by the photoelectric conversion layer 4. Therefore, noise that is generated as a result of radiation such as X-rays is effectively prevented from being absorbed by the photoelectric conversion layer 4.

It is preferred that the absorption peak wavelength of the organic photoelectric conversion material forming the photoelectric conversion layer 4 be as close as possible to the emission peak wavelength of the scintillator 8 so that the organic photoelectric conversion material most efficiently absorbs the light emitted by the scintillator 8. It is ideal that the absorption peak wavelength of the organic photoelectric conversion material and the emission peak wavelength of the scintillator 8 coincide, but as long as the difference between them is small, the organic photoelectric conversion material can sufficiently absorb the light emitted from the scintillator 8. Specifically, it is preferred that the difference between the absorption peak wavelength of the organic photoelectric conversion material and the emission peak wavelength of the scintillator 8 with respect to radiation be within 10 nm. It is more preferred that the difference be within 5 nm.

Examples of organic photoelectric conversion materials that can satisfy this condition include quinacridone organic compounds and phthalocyanine organic compounds. For example, the absorption peak wavelength in the visible range of quinacridone is 560 nm. Therefore, if quinacridone is used as the organic photoelectric conversion material and CsI(Tl) is used as the material of the scintillator 8, it is possible to make the difference between the peak wavelengths within 5 nm, and the amount of electric charge generated in the photoelectric conversion layer 4 may be substantially maximized.

Figure 4:
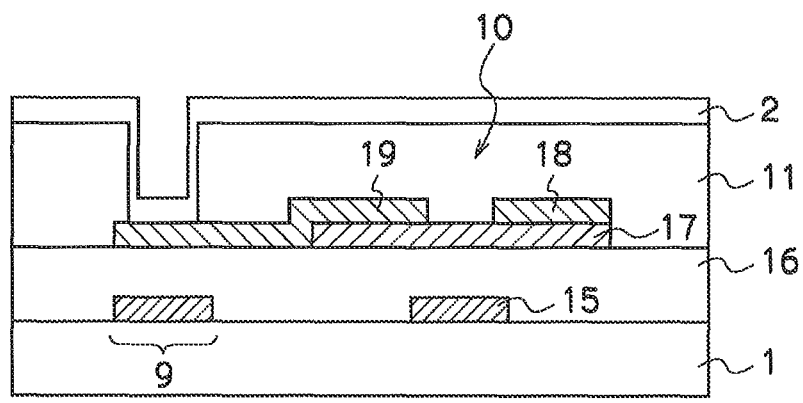
FIG. 4 a cross-sectional side view schematically illustrating the configuration of a signal output portion for a single pixel of the radiation detector.

The signal output portions 14 are formed on the surface of the substrate 1 below the lower electrodes 2 of each of the pixels. FIG. 4 schematically shows the configuration of one of the signal output portions 14.

As shown in FIG. 4, a capacitor 9 and a field-effect thin-film transistor (TFT) (hereinafter simply called as "thin-film transistor") 10 are formed in each of the signal output portions 14 in correspondence to the lower electrode 2. The capacitor 9 stores the electric charge that has moved to the lower electrode 2. The thin-film transistor 10 converts the electric charge stored in the capacitor 9 into an electric signal and outputs the electric signal. The region in which the capacitor 9 and the thin-film transistor 10 are formed has a portion that overlaps the lower electrode 2 in a plan view. Due to this configuration, the signal output portion 14 and the sensor portion 13 in each of the pixels have an overlap in the thickness direction. In order to minimize the plane area of the radiation detector 20 (the pixels), it is preferred that the region in which the capacitor 9 and the thin-film transistor 10 are formed be completely covered by the lower electrode 2.

The capacitor 9 is electrically connected to the corresponding lower electrode 2 via a wire of a conductive material penetrating an insulating film 11 that is disposed between the substrate 1 and the lower electrode 2. Because of this configuration, the electric charge trapped in the lower electrode 2 can be moved to the capacitor 9.

A gate electrode 15, a gate insulating film 16, and an active layer (channel layer) 17 are layered in the thin-film transistor 10. A source electrode 18 and a drain electrode 19 are formed a predetermined spacing apart from each other on the active layer 17.

The active layer 17 may, for example, be formed by amorphous silicon, an amorphous oxide, an organic semiconductor material, carbon nanotubes, etc. However, the material configuring the active layer 17 is not limited to these.

In a case in which the active layer 17 is configured by an amorphous oxide, oxides including at least one of In, Ga, and Zn (e.g., In—O amorphous oxides) are preferred, oxides including at least two of In, Ga, and Zn (e.g., In—Zn—O amorphous oxides, In—Ga—O amorphous oxides, or Ga—Zn—O amorphous oxides) are more preferred, and oxides including all of In, Ga, and Zn are particularly preferred. As an In—Ga—Zn—O amorphous oxide, an amorphous oxide whose composition in a crystalline state is expressed by $InGaO_3(ZnO)_m$, (where m is a natural number less than 6) is preferred, and particularly $InGaZnO_4$ is preferred.

Examples of organic semiconductor materials capable of configuring the active layer 17 include phthalocyanine compounds, pentacene, and vanadyl phthalocyanine, but the organic semiconductor materials are not limited to these. Since configurations of phthalocyanine compounds are described in detail in JP-A No. 2009-212389, descriptions thereof will be omitted here.

The generation of noise in the signal output portion 14 may be effectively prevented in a case in which the active layer 17 of the thin-film transistor 10 is formed from an amorphous oxide, an organic semiconductor material, or carbon nanotubes, since such active layer 17 does not absorb radiation such as X-rays, or even if it does absorb any radiation the absorbed radiation is an extremely minute amount.

In a case in which the active layer 17 is formed with carbon nanotubes, the switching speed of the thin-film transistor 10 is increased, and it is possible to form the thin-film transistor 10 having a low degree of absorption of light in the visible light range. In the case of forming the active layer 17 with carbon nanotubes, since the performance of the thin-film transistor 10 drops significantly even if an infinitesimal amount of a metal impurity is mixed into the active layer 17, it is necessary to separate, extract, and form extremely high-purity carbon nanotubes using centrifugal separation or the like.

Here, the amorphous oxide, organic semiconductor material, or carbon nanotubes configuring the active layer 17 of the thin-film transistor 10 and the organic photoelectric conversion material forming the photoelectric conversion layer 4 are all capable of being formed into films at a low temperature. Consequently, the substrate 1 is not limited to a substrate with high heat resistance, such as a semiconductor substrate, a quartz substrate, or a glass substrate, and a plastic or other flexible substrate, aramids, or bionanofibers may also be used. Specifically, polyester, such as polyethylene terephthalate, polybutylene phthalate, and polyethylene naphthalate, polystyrene, polycarbonate, polyethersulphone, polyarylate, polyimide, polycyclic olefin, norbornene resin, and poly(chloro-trifluoro-ethylene) or other flexible substrates may be used. By employing a flexible substrate made of plastic, the substrate may be made lightweight, which is advantageous for portability.

Further, an insulating layer for ensuring insulation, a gas barrier layer for preventing the transmission of moisture and/or oxygen, an undercoat layer for improving flatness or adhesion to the electrodes or the like, or other layers may also be disposed on the substrate 1.

Since high-temperature processes of 200 degrees or higher can be applied to aramids, a transparent electrode material can be hardened at a high temperature and given a low resistance. Aramids can also accommodate automatic packaging of driver ICs including solder reflow processes. Aramids also have a thermal expansion coefficient that is close to that of indium tin oxide (ITO) or a glass substrate, so they have little warping after manufacture and do not break easily. Further, it is possible to form a thinner substrate with aramids compared to a glass substrate or the like. An ultrathin glass substrate and an aramid may also be layered to form a substrate.

Further, bionanofibers are composites of cellulose microfibril bundles (bacterial cellulose) that a bacterium (*Acetobacter xylinum*) produces and a transparent resin. Cellulose microfibril bundles have a width of 50 nm, which is a size that is 1/10 with respect to visible wavelengths, and have high strength, high elasticity, and low thermal expansion. By impregnating and hardening a transparent resin such as an acrylic resin or an epoxy resin in bacterial cellulose, it is possible to obtain bionanofibers exhibiting a light transmittance of about 90% at a wavelength of 500 nm while including fibers at 60 to 70%. Since bionanofibers have a low thermal expansion coefficient (3 to 7 ppm) comparable to silicon crystal, a strength comparable to steel (460 MPa), high elasticity (30 GPa), and are flexible, they enable to form the substrate 1 thinner compared to a glass substrate or the like.

In the present exemplary embodiment, a TFT substrate 30 is formed by sequentially forming the signal output portions 14, the sensor portions 13, and the transparent insulating film 7 on the substrate 1, and the radiation detector 20 is formed by adhering the scintillator 8 onto the TFT substrate 30 using, for example, an adhesive resin whose light absorbance is low.

Figure 5:
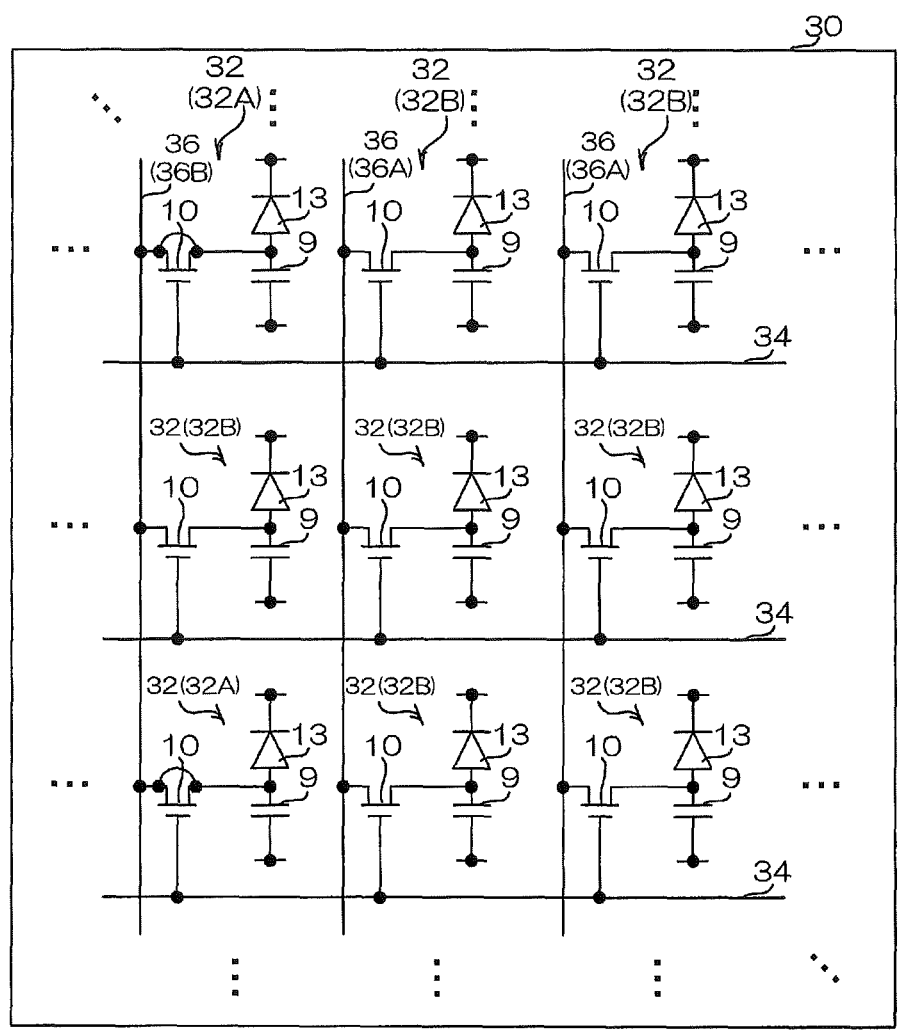
FIG. 5 is a plan view illustrating the configuration of the radiation detector.

As illustrated in FIG. 5, on the TFT substrate 30, plural pixels 32 including the sensor portions 13, the capacitors 9, and the thin-film transistors 10 are disposed two-dimensionally in one direction (a direction along gate lines 34 in FIG. 5) and an intersecting direction (a direction along signal lines 36 in FIG. 5) with respect to the one direction.

Further, plural gate lines 34 that extends in the one direction and are for switching on and off the thin-film transistors 10 and plural signal lines 36 that extends in the intersecting direction and are for reading out the electric charges via the thin-film transistors 10 that is in an on-state, are disposed in the radiation detector 20.

The radiation detector 20 is formed in a tabular, quadrilateral shape having four sides on its outer edges in a plan view. More specifically, the radiation detector 20 is formed in a rectangular shape.

In the radiation detector 20 pertaining to the present exemplary embodiment, some of the pixels 32 are used for detecting the state of irradiation with the radiation, and the remaining pixels 32 capture radiographic images. Hereinafter, the pixels 32 for detecting the state of irradiation with the radiation will be called radiation detection pixels 32A, and the remaining pixels 32 will be called radiographic imaging pixels 32B.

As illustrated in FIG. 5, the radiation detection pixels 32A according to the present exemplary embodiment are configured with thin-film transistors 10 that are each shorted across the source and drain terminals. In the radiation detection pixels 32A, the electrical charge that is being accumulated in each of the capacitors 9 accordingly flows out in the signal lines 36 irrespective of the switching state of the thin-film transistors 10.

The radiation detector 20 cannot obtain pixel information (data) of radiographic images in the positions where the radiation detection pixels 32A are placed because the radiation detector 20 captures radiographic images with the radiographic imaging pixels 32B excluding the radiation detection pixels 32A of the pixels 32. For this reason, in the radiation detector 20, the radiation detection pixels 32A are placed so as to be dispersed and the console 110 executes missing pixel correction that generates pixel data of radiographic images in the positions where the radiation detection pixels 32A are placed by interpolation using pixel data that has been obtained by the radiographic imaging pixels 32B positioned around those radiation detection pixels 32A.

Figure 6:
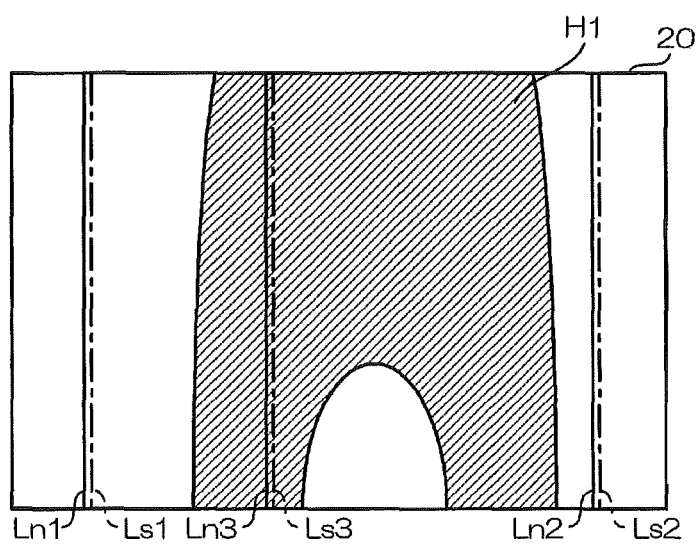
FIG. 6 is another plan view illustrating the configuration of the radiation detector.

In the radiation detector 20 according to the present exemplary embodiment, as illustrated in the example of FIG. 6, the radiation detection pixels 32A and the radiographic imaging pixels 32B are arrayed such that there are plural (three in the present exemplary embodiment) lines (arrays) Ln1, Ln2, Ln3 that only contain radiographic imaging pixels 32B (referred to below as "normal pixel lines"), and respectively adjacent plural (three in the present exemplary embodiment) lines (arrays) Ls1, Ls2, Ls3 that include radiation detection pixels 32A (referred to below as "detection pixel lines").

In the radiation detector 20 according to the present exemplary embodiment, as illustrated in the example of FIG. 6, the normal pixel lines Ln1, Ln2, Ln3 and the detection pixel lines Ls1, Ls2, Ls3 are set at three locations, these being in a region at a central portion of the imaging region of the radiation detector 20 where there is a high possibility of a subject positioned region H1, and regions at each of the two edges of the radiation detector 20 imaging region where there is a high possibility that the subject is not positioned. Note that in the radiation detector 20 according to the present exemplary embodiment, the number of radiation detection pixels 32A included in each of the detection pixel lines is a constant fixed number (20 in the present exemplary embodiment).

Figure 7:
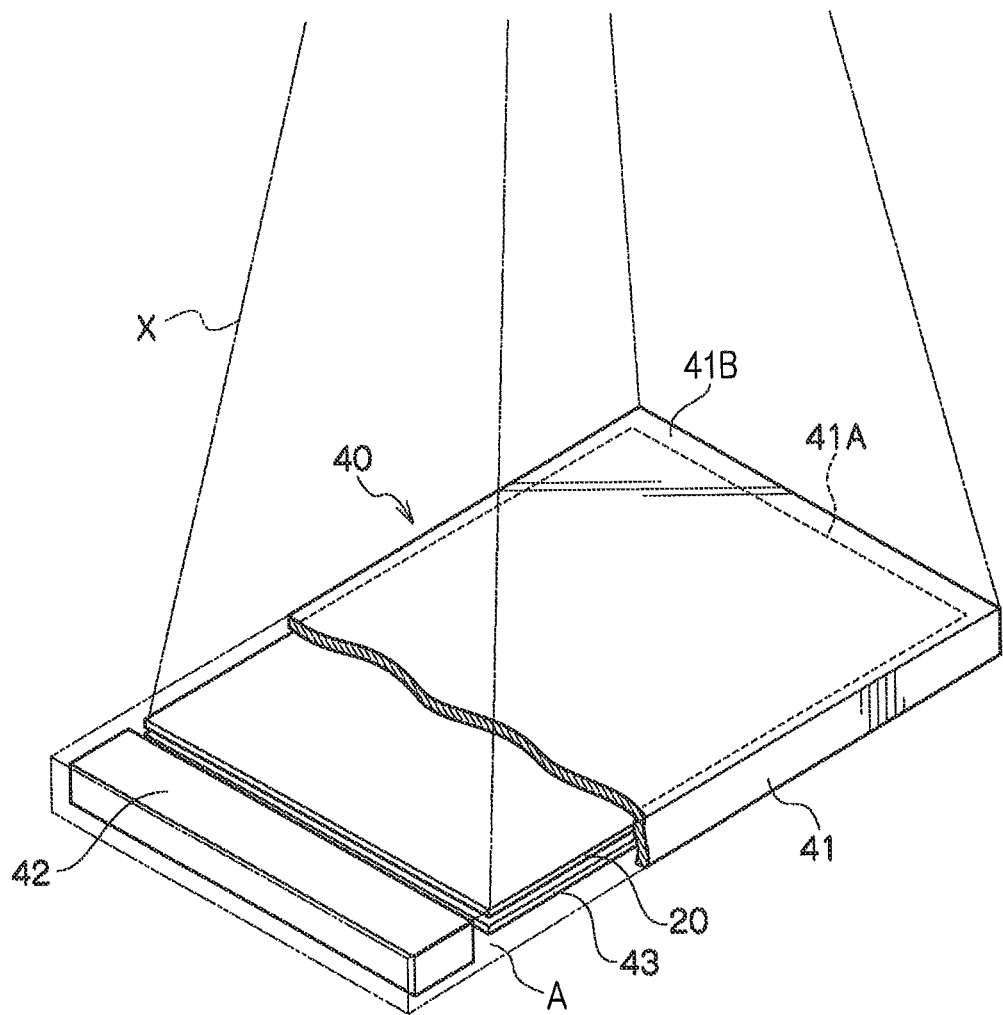
FIG. 7 is a perspective view illustrating the configuration of an electronic cassette of an exemplary embodiment.

Next, the configuration of the electronic cassette 40 pertaining to the present exemplary embodiment will be described. FIG. 7 is a perspective view illustrating the configuration of the electronic cassette 40.

As shown in FIG. 7, the electronic cassette 40 is equipped with a housing 41 that is formed from a material that allows radiation to pass through, and the electronic cassette 40 is given a waterproof and airtight structure. When the electronic cassette 40 is used in an operating room or the like, there is the concern that blood or other contaminants may adhere to the electronic cassette 40. Therefore, by giving the electronic cassette 40 a waterproof and airtight structure and disinfecting the electronic cassette 40 as needed, the single electronic cassette 40 may be used repeatedly.

A space A that accommodates various parts is formed inside the housing 41. The radiation detector 20 that detects the radiation X that has passed through the subject, and a lead plate 43 that absorbs backscattered rays of the radiation X, are disposed in this order inside the space A from a side of the housing 41 on which the radiation X is applied.

In the electronic cassette 40, the region in one surface of the tabular shape of the housing 41, which corresponds to the position at which the radiation detector 20 is disposed, is configured as a quadrilateral imaging region 41A that is capable of detecting radiation. The surface having the imaging region 41A of the housing 41 serves as a top plate 41B of the electronic cassette 40. In the electronic cassette 40, the radiation detector 20 is placed such that the TFT substrate 30 is disposed at the top plate 41B side, and the radiation detector 20 is adhered to the inner surface of the top plate 41B (the back surface of the top plate 41B at the opposite side of the surface on which the radiation is made incident) of the housing 41.

As shown in FIG. 7, a case 42 that accommodates a cassette controller 58 and a power supply section 70 (see also FIG. 9) is placed at one end side of the interior of the housing 41 in a position that does not overlap with the radiation detector 20 (i.e., outside the range of the imaging region 41A).

The housing 41 is formed of carbon fiber, aluminum, magnesium, bionanofibers (cellulose microfibrils), or a composite material, for example, in order to make the entire electronic cassette 40 lightweight.

As the composite material, for example, a material including reinforced fiber resin is used, and carbon, cellulose or the like is included in the reinforced fiber resin. Specifically, carbon fiber reinforced plastic (CFRP), a composite material with a structure where a foam material is sandwiched by CFRP, or a composite material in which the surface of a foam material is coated with CFRP may be used as the composite material. In the present exemplary embodiment, a composite material with a structure in which a foam material is sandwiched by CFRP is used. Thereby, the strength (rigidity) of the housing 41 may be raised compared to a case in which the housing 41 is configured only by a carbon.

Figure 8:
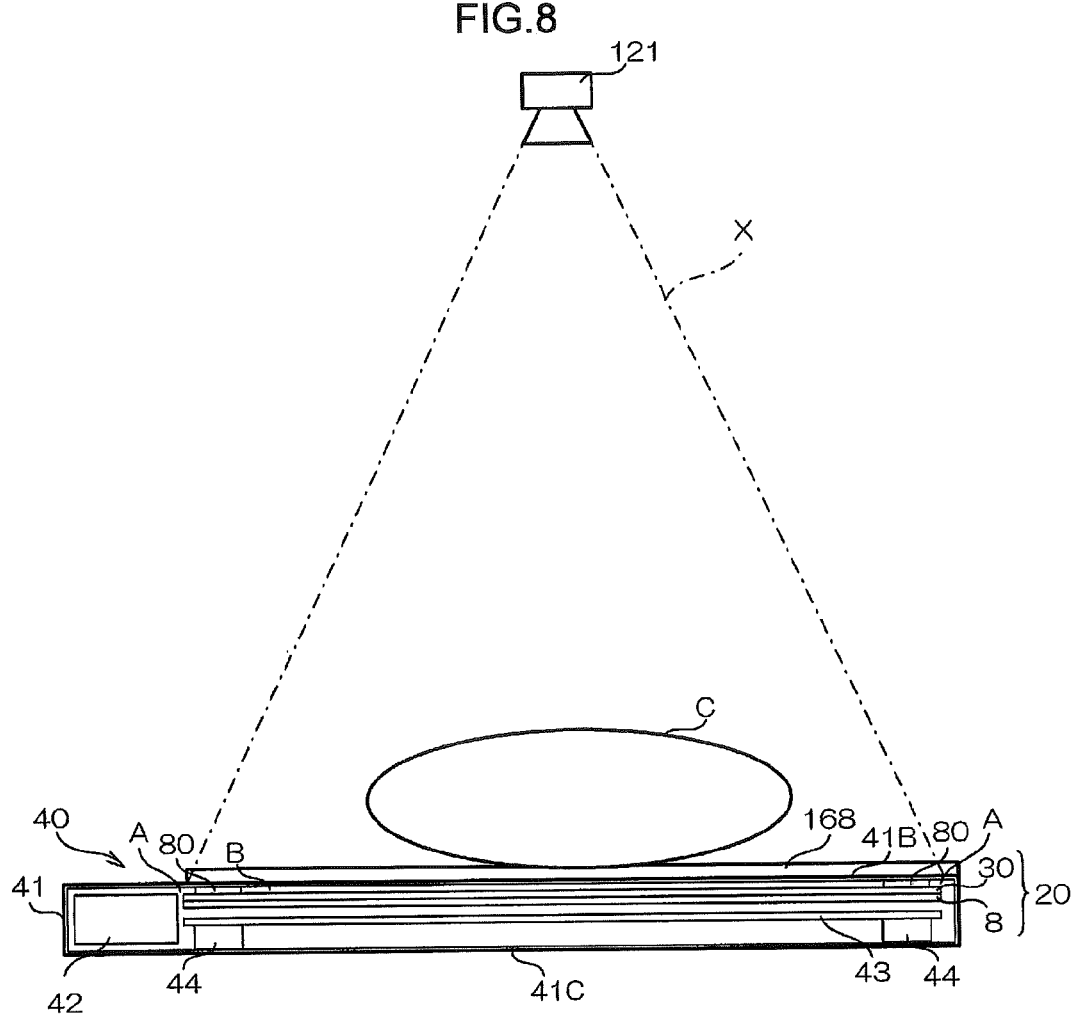
FIG. 8 is a cross-sectional side view illustrating the electronic cassette.

As shown in FIG. 8, inside the housing 41, support members 44 are disposed on the inner surface of a back surface 41C opposing the top plate 41B. The radiation detector 20 and the lead plate 43 are placed in this order in the irradiation direction of the radiation X between the support members 44 and the top plate 41B. The support members 44 that support the lead plate 43 are formed of a foam material, for example, from the standpoint of reducing weight and absorbing dimensional deviations.

As shown in FIG. 8, adhesive members 80 that detachably adhere the TFT substrate 30 of the radiation detector 20 to the top plate 41B are disposed at the inner surface of the top plate 41B. Double-sided tape, for example, may be used as the adhesive members 80. In this case, the double-sided tape 80 is formed such that the adhesive force of one adhesive surface is stronger than that of the other adhesive surface.

Specifically, the surface having a weak adhesive force (weak adhesive surface) is set to have a 180-degree peel strength equal to or less than 1.0 N/cm. The surface having a strong adhesive force (strong adhesive surface) contacts the top plate 41B, and the weak adhesive surface contacts the TFT substrate 30. Because of this configuration, the thickness of the electronic cassette 40 may be made thin compared to a case in which the radiation detector 20 is fixed to the top plate 41B by, for example, fixing members such as screws. Further, even if the top plate 41B deforms due to a shock or a load, the radiation detector 20 follows the deformation of the top plate 41B, which has high rigidity. Therefore, only deformation of large curvature (a gentle curve) arises in the radiation detector 20 and the potential for the radiation detector 20 to break due to localized deformation of low curvature can be reduced. Moreover, the radiation detector 20 may contribute to improving the rigidity of the top plate 41B.

In this way, since the radiation detector 20 is adhered to the inner surface of the top plate 41B of the housing 41 of the electronic cassette 40, the housing 41 is separable into two between the top plate 41B side and the back surface 41C side. The housing 41 may be separated into two of the top plate 41B side and the back surface 41C side when the radiation detector 20 is adhered to the top plate 41B or when the radiation detector 20 is detached from the top plate 41B.

In the present exemplary embodiment, the adhesion of the radiation detector 20 to the top plate 41B does not have to be performed in a clean room or the like. The reason is because, even if foreign materials such as metal fragments that absorb radiation have been incorporated between the radiation detector 20 and the top plate 41B, the foreign materials can be removed by detaching the radiation detector 20 from the top plate 41B.

Next, the configurations of relevant portions of an electrical system of the imaging system 104 pertaining to the present exemplary embodiment will be described with reference to FIG. 9.

Figure 9:
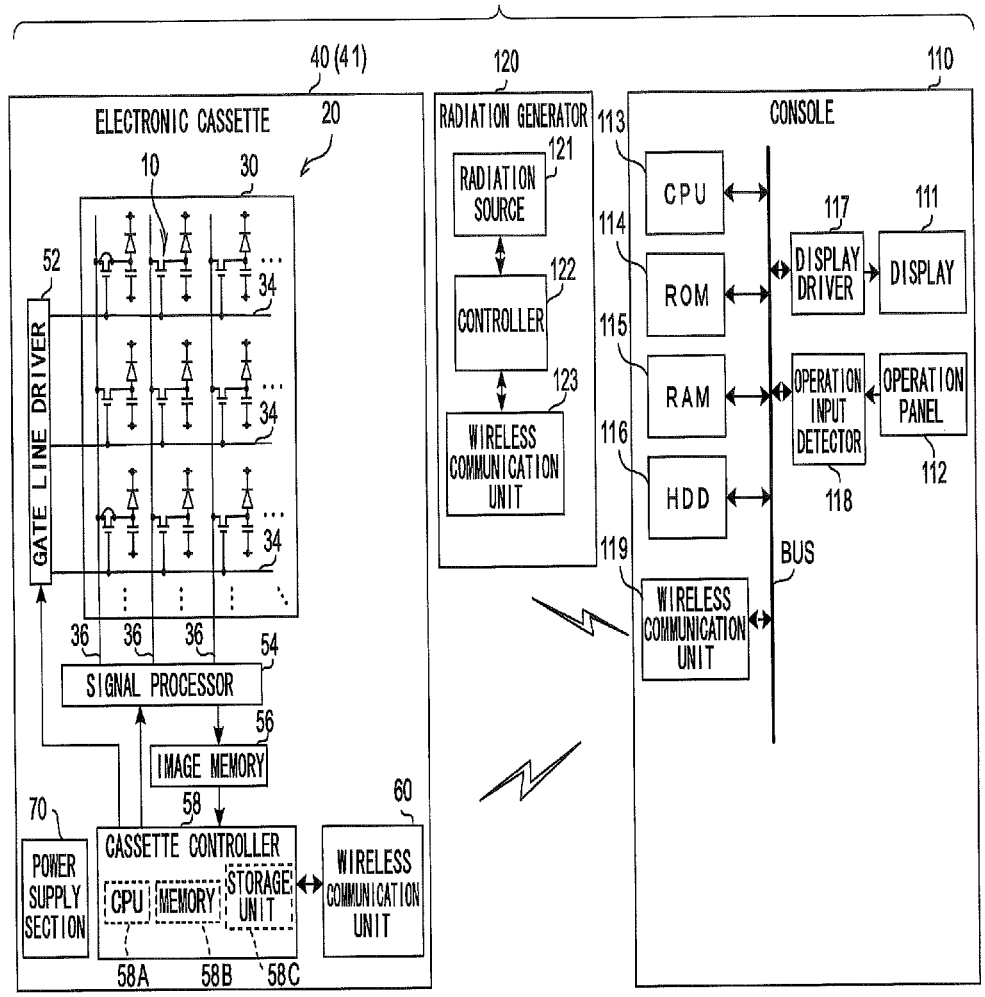
FIG. 9 is a block diagram illustrating relevant portions of an electrical system of the radiographic image capture system.

As shown in FIG. 9, in the radiation detector 20 built into the electronic cassette 40, a gate line driver 52 is placed on one side of two sides adjacent to each other, and a signal processor 54 is placed on the other side. The individual gate lines 34 of the TFT substrate 30 are connected to the gate line driver 52, and the individual signal lines 36 of the TFT substrate 30 are connected to the signal processor 54.

An image memory 56, the cassette controller 58, and a wireless communication unit 60 are disposed inside the housing 41.

The thin-film transistors 10 of the TFT substrate 30 are sequentially switched on in row units (i.e., per gate line 34) by signals supplied via the gate lines 34 from the gate line driver 52. The electric charges that have been read out by the thin-film transistors 10 switched to an on-state are transmitted through the signal lines 36 as electric signals and are inputted to the signal processor 54. Thus, the electric charges are sequentially read out per gate line 34, and a two-dimensional radiographic image is acquired.

While omitted from illustration, for every individual signal line 36 the signal processor 54 is equipped with an amplifier circuit for amplifying input electrical signals, and a sample-and-hold circuit. Electric signals transmitted by the individual signal lines 36 are held in the sample-and-hold circuits after amplification by the amplifier circuits. A multiplexer and an analog-to-digital (A/D) converter are connected in sequence to the output side of the sample-and-hold circuits. The electric signals held in the individual sample-and-hold circuits are input in sequence (serially) to the multiplexer and converted into digital image data by the A/D converter.

The image memory 56 is connected to the signal processor 54. The image data outputted from the A/D converter of the signal processor 54 are sequentially stored in the image memory 56. The image memory 56 has a storage capacity that is capable of storing image data for a predetermined number of frames' worth of radiographic images. Each time radiographic imaging is performed, the image data obtained by the imaging are sequentially stored in the image memory 56.

The image memory 56 is also connected to the cassette controller 58. The cassette controller 58 includes a microcomputer that is equipped with a central processing unit (CPU) 58A, a memory 58B including a read-only memory (ROM) and a random access memory (RAM), and a nonvolatile storage unit 58C including a flash memory or the like, and controls the operations of the entire electronic cassette 40.

Further, the wireless communication unit 60 is connected to the cassette controller 58. The wireless communication unit 60 is adapted to a wireless local area network (LAN) standard represented by IEEE (Institute of Electrical and Electronics Engineers) 802.11a/b/g/n or the like and controls the transmission of various types of information (data) between the electronic cassette 40 and external devices by wireless communication. Via the wireless communication unit 60, the cassette controller 58 is made capable of wireless communication with external devices such as the console 110 that performs control relating to radiographic imaging, and is made capable of transmitting and receiving various types of data to and from the console 110 and the like.

Further, the power supply section 70 is disposed in the electronic cassette 40. The various circuits and elements described above (the gate line driver 52, the signal processor 54, the image memory 56, the wireless communication unit 60, the microcomputer functioning as the cassette controller 58, etc.) are actuated by power supplied from the power supply section 70. The power supply section 70 has a built-in battery (a rechargeable secondary battery) so as to not impair the portability of the electronic cassette 40, and the power supply section 70 supplies power to the various circuits and elements from the charged battery. In FIG. 9, illustration of wires connecting the various circuits and elements to the power supply section 70 is omitted.

As shown in FIG. 9, the console 110 is configured as a server computer and is equipped with a display 111 that displays operation menus, captured radiographic images and so forth, and an operation panel 112 that is configured to include plural keys and by which various types of information (data) and operation instructions are inputted.

The console 110 is equipped with a CPU 113 that controls the operations of the entire device, a ROM 114 in which various programs including a control program are stored in advance, a RAM 115 that temporarily stores various types of data, a hard disk drive (HDD) 116 that stores and holds various types of data, a display driver 117 that controls the display of various types of information on the display 111, and an operation input detector 118 that detects states of operation with respect to the operation panel 112. Further, the console 110 is equipped with a wireless communication unit 119 that transmits and receives various types of information (data) such as later-described exposure conditions to and from the radiation generator 120 by wireless communication and also transmits and receives various types of information (data) such as image data to and from the electronic cassette 40 by wireless communication.

The CPU 113, the ROM 114, the RAM 115, the HDD 116, the display driver 117, the operation input detector 118, and the wireless communication unit 119 are connected to each other via a system bus BUS. Consequently, the CPU 113 is capable to access the ROM 114, the RAM 115, and the HDD 116, to control the display of various types of information on the display 111 via the display driver 117, to control the transmission and reception of various types of information (data) to and from the radiation generator 120 and the electronic cassette 40 via the wireless communication unit 119. Further, the CPU 113 is capable to grasp states of operation by a user with respect to the operation panel 112 via the operation input detector 118.

The radiation generator 120 is equipped with the radiation source 121, a wireless communication unit 123 that transmits and receives various types of information (data) such as the exposure conditions to and from the console 110, and a controller 122 that controls the radiation source 121 based on the received exposure conditions.

The controller 122 also includes a microcomputer and stores the received exposure conditions and so forth. The exposure conditions received from the console 110 include information such as tube voltage, tube current and the like. The controller 122 causes the radiation source 121 to apply the radiation X based on the received exposure conditions.

The electronic cassette 40 has a radiation determination function that determines whether or not radiation has been detected based on the values obtained by the normal pixel lines Ln1, Ln2, Ln3 and the detection pixel lines Ls1, Ls2, Ls3 of the radiation detector 20.

Explanation follows regarding the radiation determination function according to the present exemplary embodiment.

The inventors have performed the following tests in order to confirm the influence on values (referred to below as first values) representing the electrical charges that have been read from the signal lines 36 corresponding to the normal pixel lines Ln1, Ln2, Ln3 (referred to below as signal lines 36A) and on values (referred to below as second values) representing the electrical charges that have been read from the signal lines 36 corresponding to the detection pixel lines Ls1, Ls2, Ls3 (referred to below as signal lines 36B), arising in a case in which a shock is imparted and in a case in which extraneous noise from an electromagnetic field is added to the electronic cassette 40.

First, sampling of the first value and the second value is performed successively plural number of times in the case in which a shock is imparted to the electronic cassette 40 (referred to below as a first condition), in the case in which extraneous noise is applied to the electronic cassette 40 (referred to below as a second condition), and in a case in which radiation is irradiated onto the electronic cassette 40 without a shock or extraneous noise is being applied to the electronic cassette 40 (referred to below as a third condition).

Next, a histogram is generated for each of the conditions of the first to the third conditions, with values corresponding to the plural sampled first values and second values on the horizontal axis and the frequency on the vertical axis.

Figure 10:
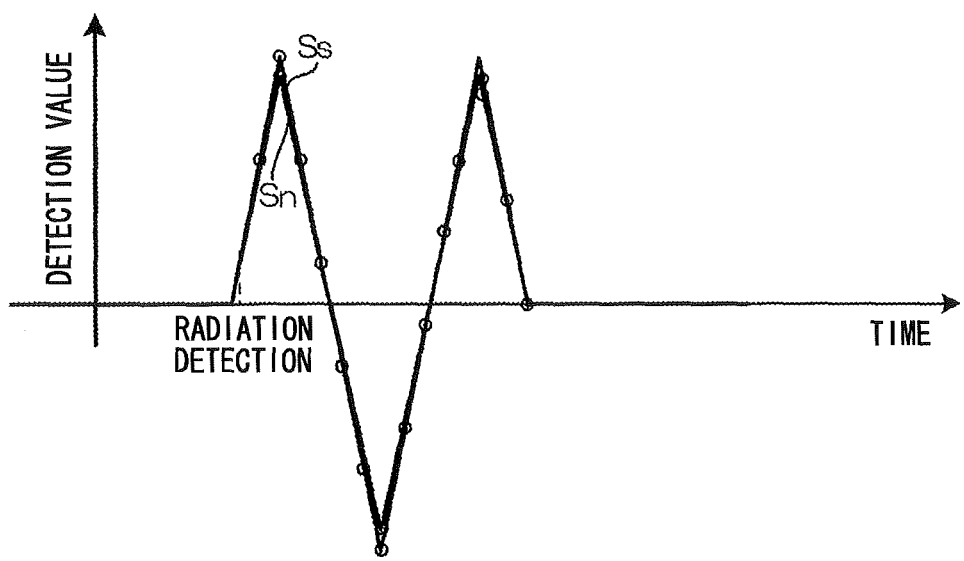
FIG. 10 is a graph illustrating an example of a relationship between elapsed time and detection values to explain a radiation determination function of an exemplary embodiment.
Figure 11:
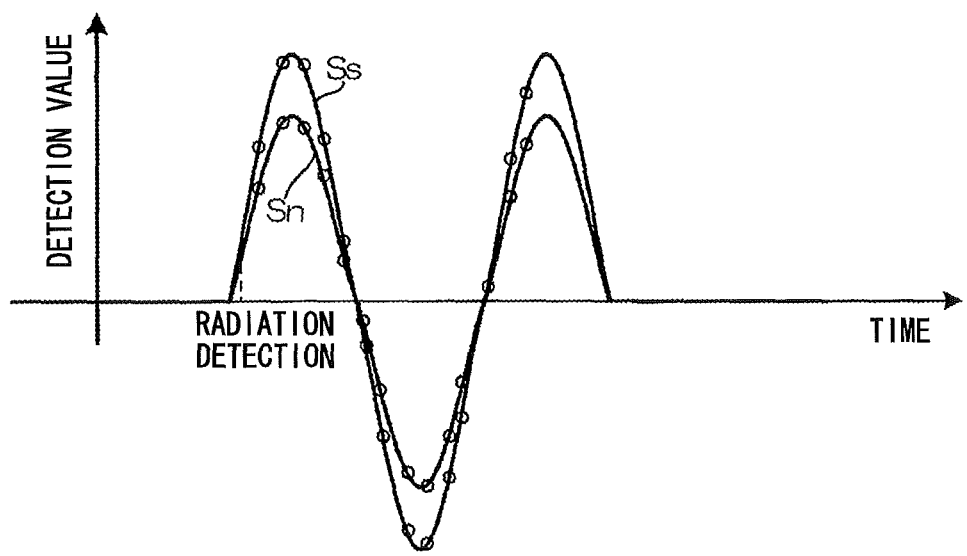
FIG. 11 is a graph illustrating an example of a relationship between elapsed time and detection values to explain the radiation determination function.
Figure 12:
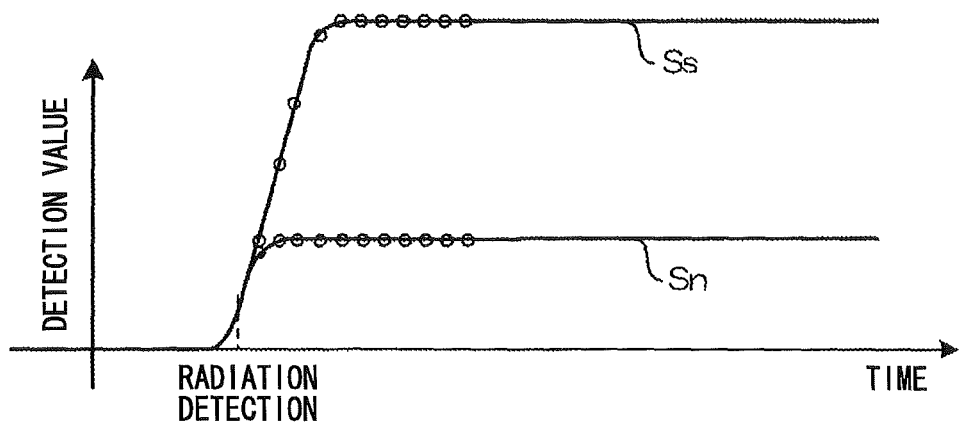
FIG. 12 is a graph illustrating an example of a relationship between elapsed time and detection values to explain the radiation determination function.

FIG. 10 illustrates an example of changes with time in the first value Sn and the second value Ss obtained under the first condition. FIG. 11 illustrates an example of changes with time in the first value Sn and the second value Ss obtained under the second condition. FIG. 12 illustrates an example of changes with time in the first value Sn and the second value Ss obtained under the third condition.

Figure 13:
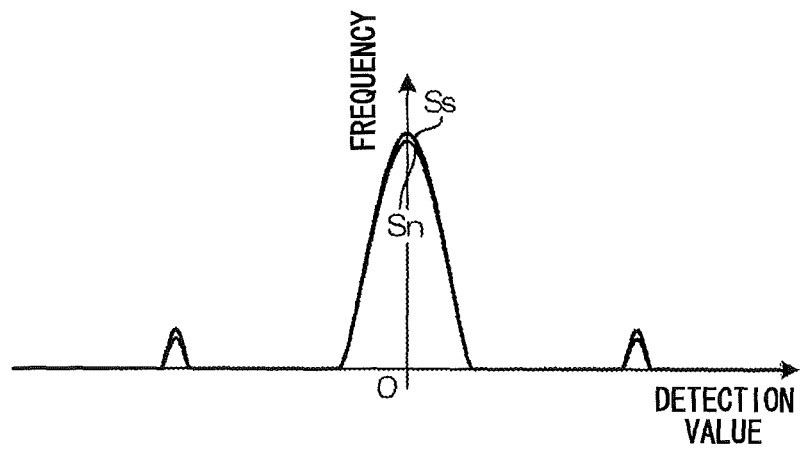
FIG. 13 is a graph illustrating an example of a relationship between detection values and frequency to explain the radiation determination function.
Figure 14:
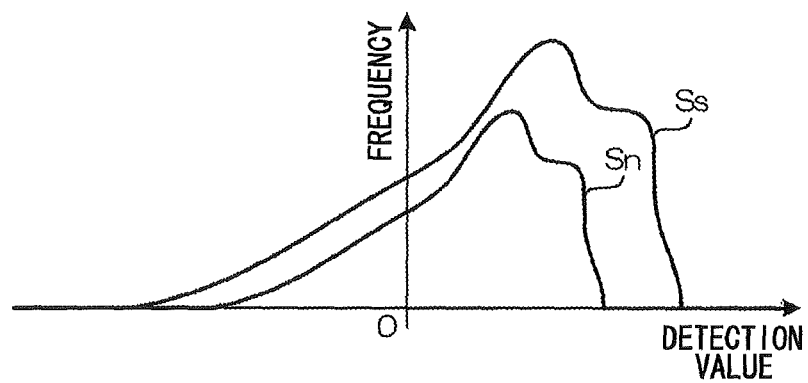
FIG. 14 is a graph illustrating an example of a relationship between detection values and frequency to explain the radiation determination function.
Figure 15:
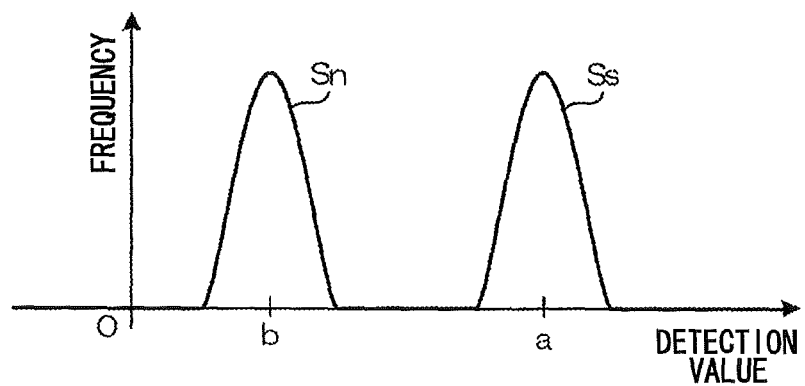
FIG. 15 is a graph illustrating an example of a relationship between detection values and frequency to explain the radiation determination function.

FIG. 13 illustrates an example of a histogram of the first value Sn and the second value Ss obtained under the first condition. FIG. 14 illustrates an example of a histogram of the first value Sn and the second value Ss obtained under the second condition. FIG. 15 illustrates an example of a histogram of the first value Sn and the second value Ss obtained under the third condition.

As is clear from these diagrams, the first values and the second values obtained under the first condition tend to show substantially matching distribution patterns. The first values and second values obtained under the second condition tend to show center of gravity positions that substantially match each other, but with different frequencies. However, the first values and the second values obtained under the third condition tend to show distributions that differ greatly from each other. Note that tests have been performed with various changes to the strength and direction for imparting shock, and to the amplitude and frequency of extraneous noise, and similar tendencies have been obtained.

The radiation determination function according to the present exemplary embodiment accordingly determines that radiation has been detected at the electronic cassette 40 if a condition is satisfied of the ratio of the second value with respect to the first value being a predetermined threshold value or greater, and otherwise determines that radiation has not been detected.

The radiation determination function according to the present exemplary embodiment employs the first value Sn and the second value Ss that have been successively sampled n times, and finally derives a first value S1 and a second value S2 by computing values obtained according to the following Equation (1) and Equation (2).

$$S1 = \sum_{i=1}^{n} Sn_i \quad (1)$$

$$S2 = \sum_{i=1}^{n} Ss_i \quad (2)$$

Then, in the radiation determination function according to the present exemplary embodiment, a ratio R is derived according to the following Equation (3), and determination is made that radiation has been detected at the electronic cassette 40 if the ratio R is a predetermined threshold value or greater, and otherwise determination is made that radiation has not been detected.

$$R = \frac{S2}{S1} \quad (3)$$

Explanation follows regarding operation of the imaging system 104 according to the present exemplary embodiment.

Figure 16:
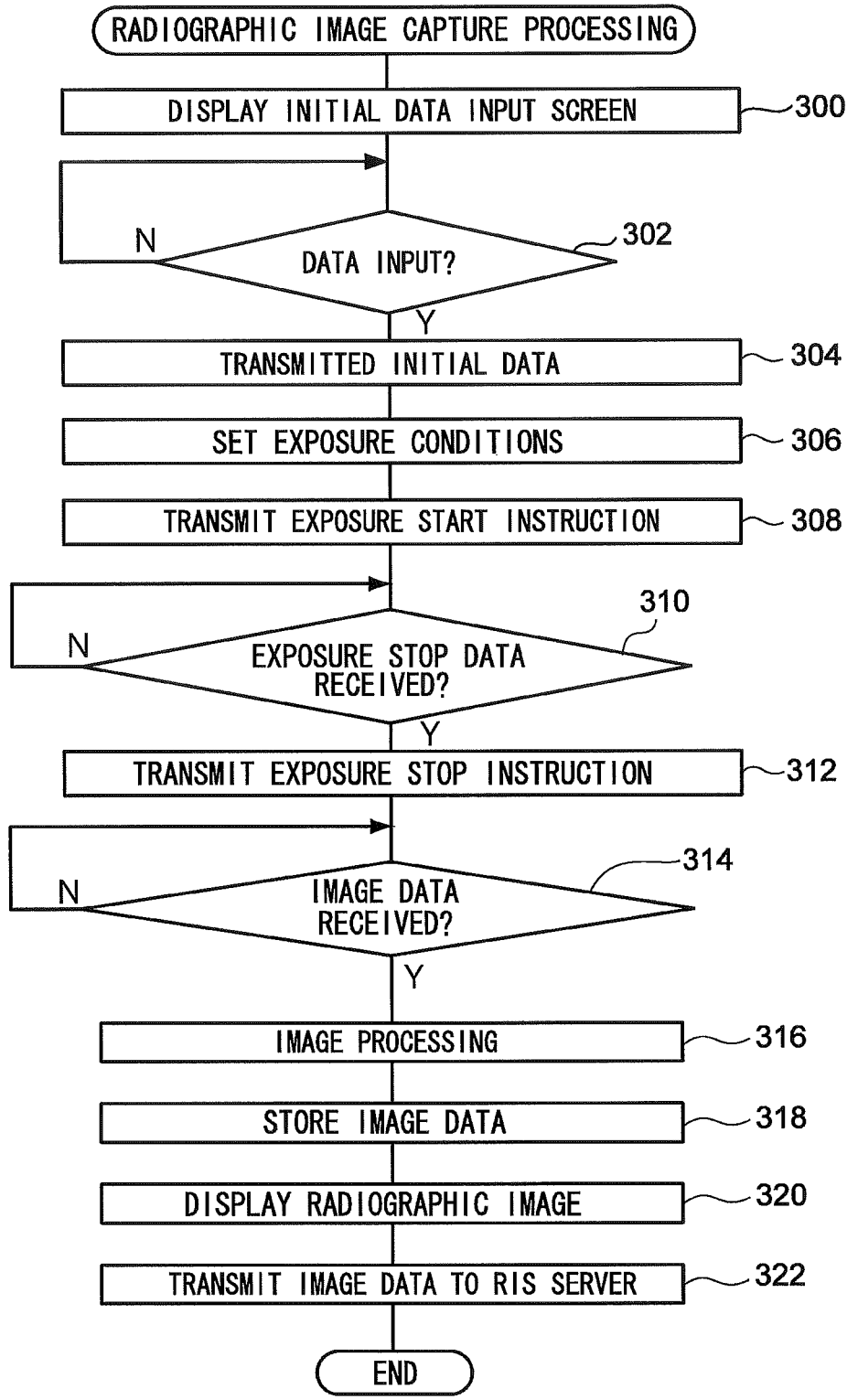
FIG. 16 is a flow chart illustrating the flow of processing of a radiographic image capture program according to an exemplary embodiment.

First explanation follows regarding operation of the console 110 when capturing a radiographic image, with reference to FIG. 16. FIG. 16 is a flow chart illustrating a flow of processing in a radiographic image capture processing program executed by the CPU 113 of the console 110 in a case in which an execution instruction has been input to the console 110 using the operation panel 112. The program is installed in a specific region of the ROM 114.

At step 300 of FIG. 16, the CPU 113 controls the display driver 117 so as to display a predetermined initial data input screen on the display 111, and then stands by at the next step 302 for specific data input.

FIG. 17 illustrates an example of the initial data input screen displayed on the display 111 by the processing of step 300. As illustrated in FIG. 17, the initial data input screen according to the present exemplary embodiment displays a message to prompt input of the name of a subject for radiographic image capture, imaging target site, posture during imaging, and exposure conditions of radiation X during imaging (in the present exemplary embodiment, tube voltage and tube current during radiation X emission), and displays input fields for such data.

After the initial data input screen illustrated in FIG. 17 has been displayed by the display 111, the imaging technician (user) may input the name of the subject for image capture, the imaging target site, the posture for image capture and the exposure conditions to each corresponding input field using the operation panel 112.

Then the imaging technician may enter the radiographic imaging room 180 together with the subject, and after retaining the electronic cassette 40 on the holding unit 162 of the standing position stand 160 or the holding unit 166 of the lying position table 164 corresponding respectively to standing or prone posture during imaging and positioning the radiation source 121 in a corresponding position, the imaging technician may then position the subject in a specific imaging position. In a case in which a radiographic image for an imaging target site such as an arm region or leg region is to be captured with the electronic cassette 40 not retained by a holding unit, the imaging technician may position the subject, the electronic cassette 40 and the radiation source 121 in a state in which the imaging target site can be captured.

Then, the imaging technician may leave the radiographic imaging room 180 and indicate completion of setting by operating the complete button displayed in the vicinity of the bottom edge of the initial data input screen using the operation panel 112. If the complete button has been instructed by the imaging technician, affirmative determination is made at step 302 and processing transitions to step 304.

At step 304, the console 110 transmits data (referred to below as initial data) that has been input to the initial data input screen to the electronic cassette 40 using the wireless communication unit 119. Then at the next step 306 the console 110 transmits the exposure conditions contained in the initial data to the radiation generator 120 using the wireless communication unit 119 and sets the exposure conditions to the radiation generator 120. In response, the controller 122 of the radiation generator 120 performs exposure preparation with the received exposure conditions.

At the next step 308, the console 110 transmits instruction data instructing initiation of exposure to the radiation generator 120 and the electronic cassette 40 using the wireless communication unit 119.

In response, the radiation source 121 starts emitting the radiation X with the tube voltage and tube current corresponding to the exposure conditions that the radiation generator 120 have received from the console 110. The radiation X emitted from the radiation source 121 arrives at the electronic cassette 40 after passing through the subject.

Meanwhile, on receipt of the instruction data instructing initiation of exposure, the cassette controller 58 of the electronic cassette 40 switches the thin-film transistors 10 of all the radiation detector 20 into the ON state, and stands by until an amount of radiation obtained based on image data stored in the image memory 56 according to the electrical charges read from each of the signal lines 36 (referred to below as "radiation detection image data") reaches a predetermined threshold value or greater, where predetermined threshold value is a value for detecting that radiation irradiation has started. The electronic cassette 40 then determines whether or not the detected amount of radiation indicates irradiation of actual radiation using the previously described radiation determination function. Radiographic image capture operation is performed only in cases in which it is determined that radiation is applied, and then the electronic cassette 40 transmits exposure stop data instructing termination of radiation X exposure to the console 110.

The console 110 stands by at the next step 310 for receipt of the exposure stop data. At the next step 312, the console 110 transmits instruction data instructing termination of radiation X exposure to the radiation generator 120 using the wireless communication unit 119. In response radiation X exposure from the radiation source 121 is stopped.

After the radiographic image capture operation is stopped, the electronic cassette 40 transmits the image data obtained by image capture to the console 110.

The console 110 stands by at the next step 314 for receipt of the image data from the electronic cassette 40, and at the next step 316 the console 110 subjects the received image data to the missing pixel correction processing, and then executes image processing to perform various types of correction, such as shading correction.

At the next step 318, the console 110 stores the image data (referred to below as "corrected image data") to which the above image processing has been performed in the HDD 116. Then at the next step 320, the console 110 effects control of the display driver 117 to display a radiographic image expressed by the corrected image data on the display 111 for verification.

At the next step 322, the console 110 transmits the corrected image data to the RIS server 150 via the in-hospital network 102, and then the radiographic image capture processing program ends. The corrected image data transmitted to the RIS server 150 may be stored in the database 150A, enabling a doctor to perform for example reading of the captured radiographic image and diagnosis.

Figure 18:
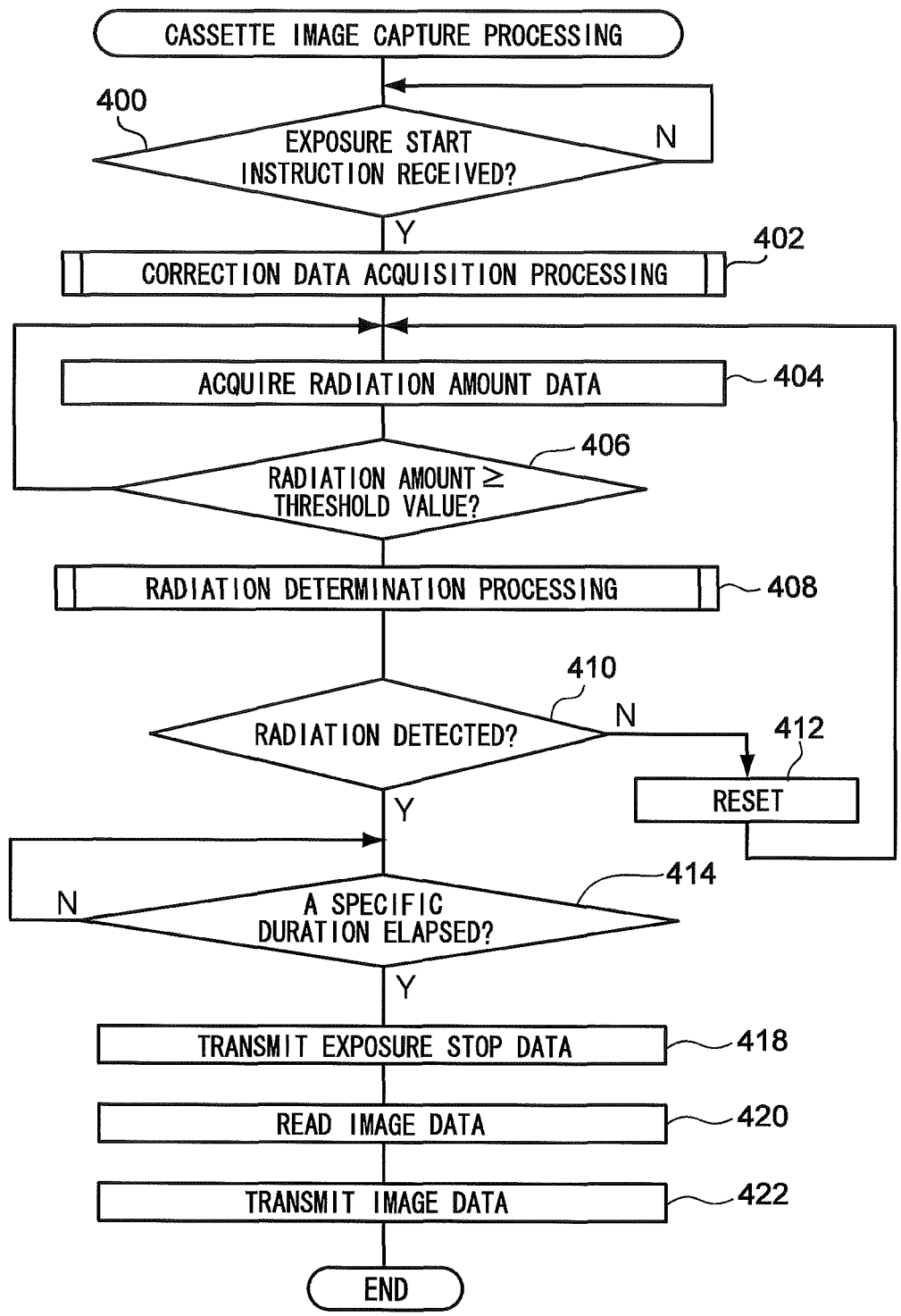
FIG. 18 is a flow chart illustrating flow of processing of a cassette image capture program according to an exemplary embodiment.

Explanation follows regarding operation of the electronic cassette 40 after receiving the initial data from the console 110, with reference to FIG. 18. FIG. 18 is a flow chart illustrating a flow of processing in a cassette image capture processing program executed at this stage by the CPU 58A in the cassette controller 58 of the electronic cassette 40. The program is installed in a specific region of the memory 58B.

At step 400 in FIG. 18, the electronic cassette 40 is on reception standby for the instruction data from the console 110 instructing initiation of exposure, and at the next step 402 a correction data acquisition processing routine program is executed.

Figure 19:
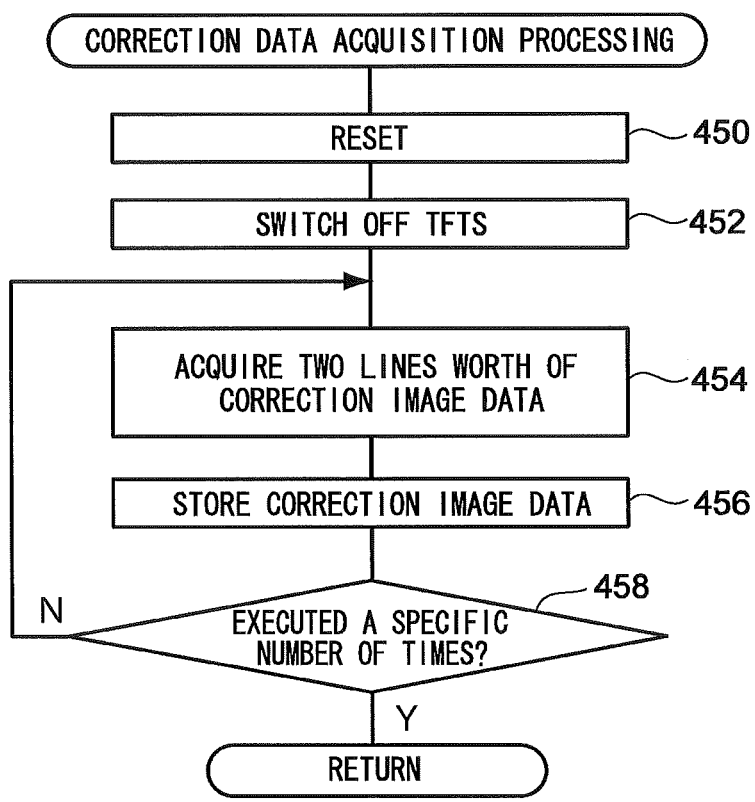
FIG. 19 is a flow chart illustrating a flow of processing of a correction data acquisition processing routine program.

Explanation follows regarding the correction data acquisition processing routine program according to the present exemplary embodiment, with reference to FIG. 19. FIG. 19 is a flow chart illustrating a flow of processing of the correction data acquisition processing routine program. The program is also installed in a specific region of the memory 58B.

At step 450 in FIG. 19 the cassette controller 58 resets the radiation detector 20 by effecting control of the gate line driver 52 to switch all of the thin-film transistors 10 to an ON state. At the next step 452, the cassette controller 58 controls the gate line driver 52 to switch all of the thin-film transistors 10 to an OFF state.

At the next step 454, the cassette controller 58 acquires image data (referred to below as "correction normal line image data") based on electrical charge read from one of the signal lines 36A and image data (referred to below as "correction detection line image data") based on electrical charge read from one of the signal lines 36B by reading from the image memory 56. Then at the next step 456, the cassette controller 58 stores the acquired correction normal line image data and correction detection line image data in a specific region of the memory 58B.

At the next step 458, the cassette controller 58 determines whether or not the processing of the above step 454 to step 456 has been performed n times. If negative determination is made processing returns to step 454, and if affirmative determination is made, the correction data acquisition processing routine program is ended. Note that during repeatedly execution of step 454 to step 458, the correction normal line image data and correction detection line image data that are acquired at step 454 are stored in different respective storage regions so that the time sequence of the acquired data can be identified.

The correction data acquisition processing routine program is a program for acquiring data (referred to below as correction normal line image data and correction detection line image data) used in offset correction processing and fixed noise reduction correction processing that are performed in a radiation determination processing routine program (FIG. 20) described later. The offset correction processing is a processing for reducing the influence of electrical charges due to dark current that occurs in the radiation detector 20 and reducing the influence of switching noise that occurs when the thin-film transistors 10 are switched. The fixed noise reduction correction processing is a processing for reducing fixed noise that inherently occurs according to the array position of the respective pixels 32.

In the radiation determination processing routine program according to the present exemplary embodiment, as described below, radiation detection image data that has been sampled n times from the start point when all of the thin-film transistors 10 are switched to the OFF state, is cumulatively summed. The ratio R is computed based on the thus obtained cumulative radiation detection image data. Hence, when the processing of step 454 to step 458 of the correction data acquisition processing routine program is repeatedly executed, the timings at which the correction normal line image data and the correction detection line image data are acquired by the processing of step 454 are set to be substantially the same timing, when acquiring the radiation detection image data in the radiation determination processing routine program, from the start point at which all of the thin-film transistors 10 are switched to the OFF state.

After the correction data acquisition processing routine program is ended, the processing returns to step 404 of the cassette image capture processing program (main routine). At step 404, after the cassette controller 58 has controlled the gate line driver 52 so as to switch all of the thin-film transistors 10 to the ON state, the image data that is accordingly stored in the image memory 56 (radiation detection image data) is read and combined to acquire data representing the amount of radiation (referred to below as radiation amount data).

At the next step 406, the cassette controller 58 determines whether or not the amount of radiation expressed by the radiation amount data acquired by the processing of step 404 is the threshold value or greater. If negative determination is made, processing returns to step 404. However, if affirmative determination is made at step 406, it is determined that the radiation X exposure from the radiation source 121 has started, and processing transitions to step 408.

At step 408 the radiation determination processing routine program is executed.

Figure 20:
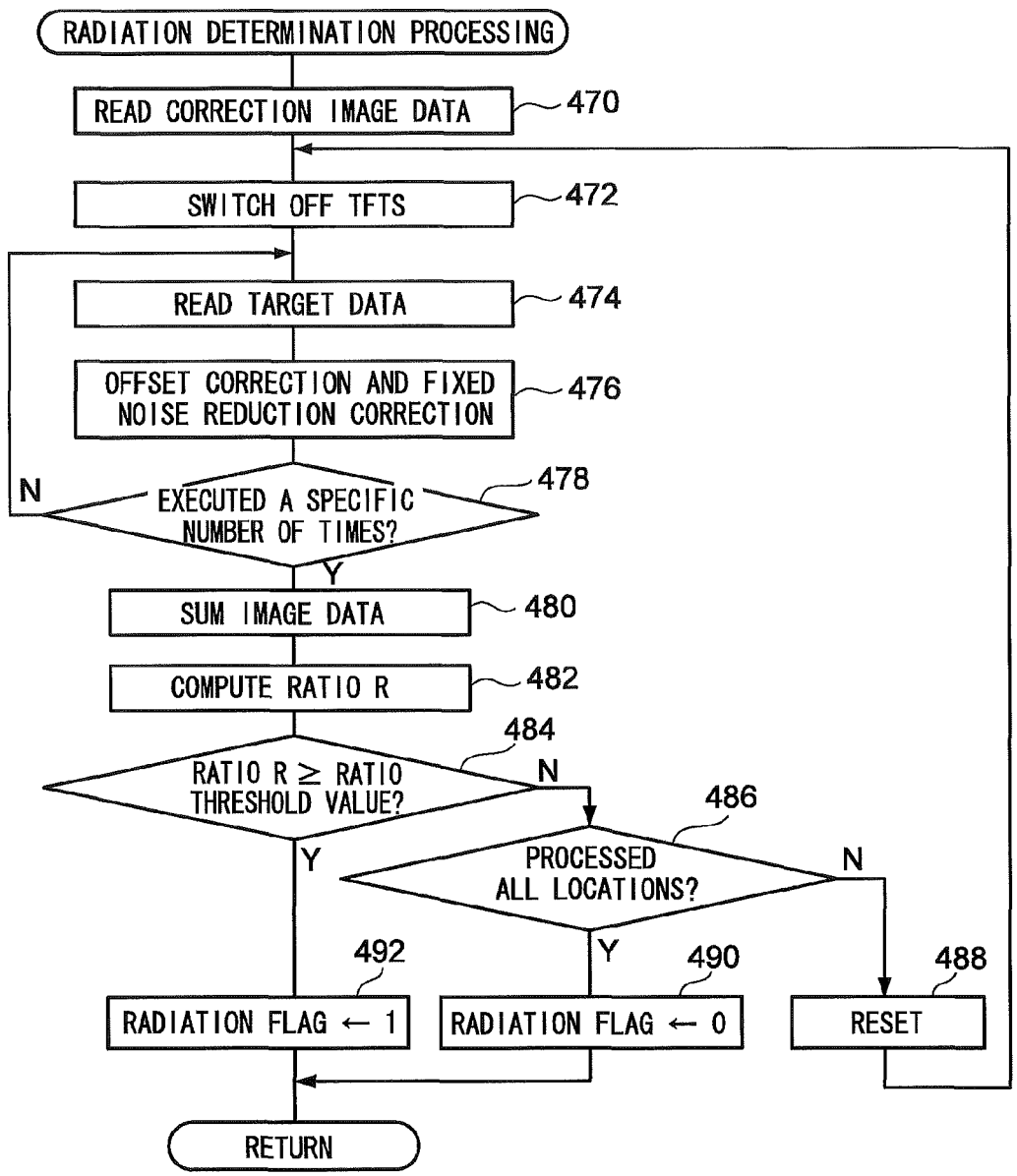
FIG. 20 is flow chart illustrating a flow of processing of the radiation determination processing routine program.

Explanation follows regarding the radiation determination processing routine program according to the present exemplary embodiment with reference to FIG. 20. FIG. 20 is a flow chart illustrating a flow of processing of the radiation determination processing routine program. The program is installed in a specific region of the memory 58B.

At step 470 in FIG. 20, the cassette controller 58 reads the correction normal line image data and the correction detection line image data from the memory 58B. At the next step 472, the cassette controller 58 controls the gate line driver 52 such that all of the thin-film transistors 10 are switched to the OFF state.

At the next step 474, image data obtained from the signal line 36A corresponding to one line out of the normal pixel lines Ln1, Ln2, Ln3 (referred to below as target normal image data) and image data obtained from the signal line 36B corresponding to the adjacent one line of the detection pixel lines Ls1, Ls2, Ls3 (referred to below as target detection image data) is read from the image memory 56.

At the next step 476, offset correction processing and fixed noise reduction correction processing are performed by subtracting the correction normal line image data from the target normal image data, and subtracting the correction detection line image data from the target detection image data. The resultant modified target normal image data and modified target detection image data is stored in a specific region of the memory 58B.

At the next step 478, the cassette controller 58 determines whether or not the processing of step 474 to step 476 has been executed n times. If negative determination is made, processing returns to step 474, and if affirmative determination is made, processing transitions to step 480. During repetition of step 474 to step 478, the subtractions at step 476 are performed employing the correction normal line image data and the correction detection line image data that have been obtained at substantially the same timings with respect to start point when all of the thin-film transistors 10 are switched to the OFF state.

At step 480, the cassette controller 58 reads from the memory 58B the modified target normal image data and the modified target detection image data that have been stored by the processing of step 476, and sums the respective set of data. In the present exemplary embodiment, the data subject to summing by the processing of step 480 is limited to data that falls in a predetermined range. However, this is not a limitation and the summation may be performed without such a limitation. Examples of the predetermined range include a range specified by predetermined fixed values according to various conditions such as the type of the radiation detector 20 and the environmental temperature, and a range in a histogram for example as illustrated in FIG. 13 excluding any values separated from the central value by a specific value or greater.

At the next step 482, the ratio R is computed according to Equation (3) using the summed target normal image data obtained by the above processing as the first value S1, and the summed target detection image data as the second value S2.

At the next step 484, the cassette controller 58 determines whether or not the ratio R is a predetermined threshold value (referred to below as "radiation detection threshold value") or greater, and if negative determination is made, processing transitions to step 486. At step 486, determination is made as to whether or not the processing of step 484 has been completed for all the adjacent combinations of the normal pixel lines Ln1, Ln2, Ln3 and the detection pixel lines Ls1, Ls2, Ls3. If negative determination is made, processing transitions to step 488, the cassette controller 58 controls the gate line driver 52 so as to switch all the thin-film transistors 10 to the ON state, thereby resetting the radiation detector 20 before processing returns to step 472. If affirmative determination is made at step 486, processing transitions to step 490. During repetition of step 472 to step 488, a different combination of the normal pixel lines Ln1, Ln2, Ln3 and the detection pixel lines Ls1, Ls2, Ls3, which has not previously been subject to the processing, is employed at step 474.

The radiation detection threshold value is a value to discriminate between the ratio R provided in a state not imparted with shock or extraneous noise and the ratio R provided in a state imparted with shock or extraneous noise, which may be obtained by tests performed in advance using the real device (electronic cassette 40) as a test device, or by computer simulation based on such factors as the design specification of the electronic cassette 40.

At step 490, a value representing determination that radiation has not been detected ("0" in the present exemplary embodiment) is substituted as a radiation flag representing whether or not radiation has been detected, and then the radiation determination processing routine program is ended.

If negative determination is made at step 484, processing transitions to step 494, and a value representing determination that radiation has been detected ("1" in the present exemplary embodiment) is substituted as the radiation flag. The radiation determination processing routine program is then ended.

When the processing of the radiation determination processing routine program is ended, processing returns to step 410 of the cassette image capture processing program (main routine).

At step 410, the cassette controller 58 determines whether or not the determination in the radiation determination processing routine program was that radiation has been detected by referring to the value of the radiation flag. If negative determination is made, the cassette controller 58 determines that any detection made was due to the influence of shock or extraneous noise and processing transitions to step 412. At step 412 the cassette controller 58 controls the gate line driver 52 so as to switch all of the thin-film transistors 10 to the ON state in order to reset the radiation detector 20, and then processing returns to step 404. However, if affirmative determination is made at step 410, processing transitions to step 414.

At the next step 414, the cassette controller 58 waits for a predetermined duration to elapse as an appropriate imaging duration according to such factors as the imaging target site and the imaging conditions. At the next step 418, the cassette controller 58 transmits the exposure stop data to the console 110 using the wireless communication unit 60.

At the next step 420, the cassette controller 58 controls the gate line driver 52 such that an ON signal is output in sequence one line at a time from the gate line driver 52 to each of the gate lines 34, thereby switching ON each of the thin-film transistors 10 connected to each of the gate lines 34 one line at a time.

In the radiation detector 20, when each of the thin-film transistors 10 connected to each of the gate lines 34 is switched ON in sequence one line at a time, the electrical charges that have been accumulated in the capacitors 9 flow out of the respective signal line 36 as electrical signals, one line at a time. The electrical signals that flow out of each of the signal lines 36 are converted into digital image data by the signal processor 54, and stored in the image memory 56.

At step 420, the cassette controller 58 reads the image data stored in the image memory 56, and at the next step 422 the cassette controller 58 transmits the read image data to the console 110 using the wireless communication unit 60, and then ends the cassette image capture processing program.

The electronic cassette 40 according to the present exemplary embodiment is installed with the radiation detector 20 such that the radiation X is irradiated from the TFT substrate 30 side as illustrated in FIG. 8.

Figure 21:
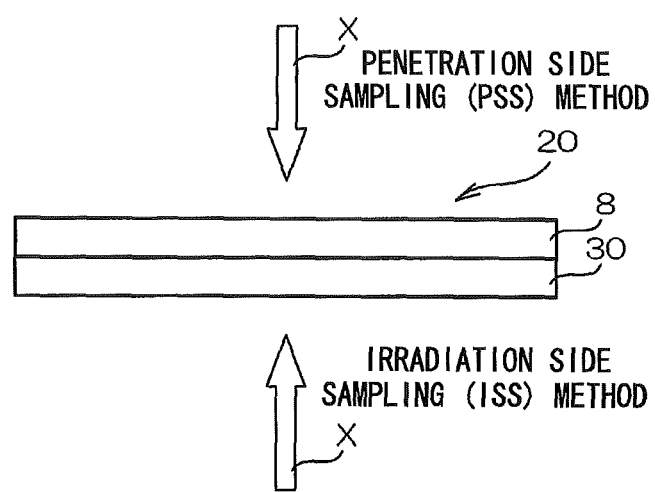
FIG. 21 is a cross-sectional side view for explaining radiographic imaging using an Irradiation Side Sampling (ISS) method and a Penetration Side Sampling (PSS) method.

In a case in which a Penetration Side Sampling (PSS) method is employed, in which the radiation detector 20 is irradiated with radiation from the side where the scintillator 8 is formed, as illustrated in FIG. 21, and radiographic images are read by the TFT substrate 30 provided on the back face side with respect to the radiation incident face, light is emitted with higher intensity at the top side of the scintillator 8 in FIG. 21 (the opposite side to the TFT substrate 30). However, in a case in which an Irradiation Side Sampling (ISS) method is employed, in which radiation is irradiated from the TFT substrate 30 side and a radiographic image is read by the TFT substrate 30 provided at the radiation incident side, since radiation is made incident to the scintillator 8 through the TFT substrate 30, light is emitted with higher intensity at the TFT substrate 30 side of the scintillator 8. Each of the sensor portions 13 provided in the TFT substrate 30 generates electrical charges due to the light generated by the scintillator 8. The radiation detector 20 therefore gives a higher resolution of captured radiographic images in a case in which an ISS method is employed than a case in which a PSS method is employed, since the most intense light emission position of the scintillator 8 is closer to the TFT substrate 30.

The radiation detector 20 is configured with the photoelectric conversion layer 4 formed from an organic photoelectric conversion material and, therefore, radiation is barely absorbed by the photoelectric conversion layer 4. In the radiation detector 20 according to the present exemplary embodiment, the amount of radiation absorbed by the photoelectric conversion layer 4 is accordingly low even through radiation passes through the TFT substrate 30 in a case of employing an ISS method. Any drop in sensitivity to radiation can hence be suppressed. Although in an ISS method radiation reaches the scintillator 8 after passing through the TFT substrate 30, if the photoelectric conversion layer 4 of the TFT substrate 30 is configured by an organic photoelectric conversion material, it is suitable for an ISS method since hardly any radiation is absorbed in the photoelectric conversion layer 4 and radiation attenuation can be reduced to a small amount.

Further, both the amorphous oxide material configuring the active layer 17 of the thin-film transistors 10 and the organic photoelectric conversion material configuring the photoelectric conversion layer 4 are possible to be formed in to a film at low temperature. The substrate 1 can accordingly be formed from plastic resin, aramid and/or bionanofibers, having low absorptivity to radiation. Since the amount of radiation absorbed by the thus formed substrate 1 is small, it is possible to prevent the sensitivity to radiation from falling even in cases of employing an ISS method in which radiation passes through the TFT substrate 30.

As illustrated in FIG. 8, in the present exemplary embodiment, the radiation detector 20 is attached to the top plate 41B inside the housing 41 such that the TFT substrate 30 is disposed at the top plate 41B side. In this regard, if the substrate 1 is formed from a high rigidity plastic resin, aramide and/or bionanofibers, since the rigidity of the radiation detector 20 becomes high, the top plate 41B of the housing 41 can be formed thinner. Further, if the substrate 1 is formed from a high rigidity plastic resin, aramide and/or bionanofibers, since the radiation detector 20 is also given flexibility, the radiation detector 20 is not readily damaged even if a shock is imparted to the imaging region 41A.

As explained in detail above, in the present exemplary embodiment, it is determined that radiation is detected at the electronic cassette 40 if a condition that the ratio (the ratio R in the present exemplary embodiment) of the second value with respect to the first value being the predetermined threshold value or greater. The first value represents electrical charge reads from the first signal lines provided for lines containing only the radiographic imaging pixels (the signal lines 36A in the present exemplary embodiment), and the second value represents electrical charge reads from the second signal lines provided for lines containing the radiation detection pixels (the signal lines 36B in the present exemplary embodiment), wherein the reading of the electric charges from the first lines and the second lines are performed after all the switching elements (the thin-film transistors 10 in the present exemplary embodiment) are switched OFF. Radiation can accordingly be detected at high precision irrespective of the irradiation amount of radiation.

Moreover, radiation can be detected at high precision in the present exemplary embodiment since offset correction is performed on the first value and the second value in order to reduce the influence of electrical charge due to dark current and to reduce the influence of switching noise that occurs when the switching elements are switched.

Moreover, radiation can be detected at high precision in the present exemplary embodiment since fixed noise reduction correction is performed on the first value and the second value to reduce the influence of fixed noise.

Moreover, in the present exemplary embodiment, the determination is performed using the summed value representing the electrical charges read successively the predetermined number of times from the first signal lines as the first value and the summed value representing the electrical charges read successively the predetermined number of times from the second signal lines as the second value. Consequently, radiation can be detected at higher precision than in cases in which such summation is not performed.

In particular, in the present exemplary embodiment, the values subject to summation fall within a predetermined range. As a result influence from such factors as unexpected noise can be reduced, and radiation irradiation start can be detected with higher precision.

Moreover, in the present exemplary embodiment, the determination is performed plural times using different combinations of the first value and the second value, and the determination is made that radiation has been detected at the electronic cassette once any single combination of the plural combinations satisfies the condition, and otherwise the determination is made that radiation has not been detected. That is, a positive determination is made if the number of combinations satisfying the condition is a second threshold value (1 in the present exemplary embodiment) or greater. Consequently, radiation detection can be performed with higher precision than in cases in which the determination is performed using only one combination. Note that the second threshold value is not limited to 1 as adopted in the present exemplary embodiment, and may be greater than 1 depending on specific applications.

In the present exemplary embodiment, the determination is made using the first value and the second value representing the electrical charges read from the first signal line and the second signal line that are adjacent. As a result, since the determination can be performed employing values obtained under substantially the same condition for each of various conditions, such as temperature, load, and extraneous noise, radiation detection can be performed with higher precision.

Furthermore, in the present exemplary embodiment, the electronic cassette is controlled to transition to capture operation of a radiographic image using the radiation detector, after it is determined that radiation has been detected at the electronic cassette. As a result radiation can be detected with higher precision, and it is possible to avoid capture of unnecessary radiographic images due to misdetection.

Note that the technical scope of the present invention is not limited by the scope of the exemplary embodiment described above. Various modifications and improvements may be made to the above exemplary embodiment within a scope not departing from the spirit of the present invention, and such modifications and improvements fall within the technical scope of the present invention.

The above exemplary embodiment does not limit the invention as recited in the claims, and not all of the combination of the features explained in the above exemplary embodiment are required to realize the solution of the invention. The above exemplary embodiment includes various levels of invention, and various aspects of the invention can be obtained by suitable combinations of plural configuration elements described herein. As long as the effect can be obtained, a number of the configuration elements may be omitted from the total configuration described in the exemplary embodiment, and such configuration with omitted configuration element(s) still falls within the scope of the invention.

For example, explanation has been given in the above exemplary embodiment in which, after the start of radiation irradiation has been detected, the determination is made by the radiation determination function as to whether or not the detected amount indicates irradiation of radiation. However, exemplary embodiments are not limited thereto and, for example, an embodiment may be configured such that the start of radiation irradiation is also detected by the radiation determination function. In this case, the processing of step 404 and step 406 may be eliminated from the cassette image capture processing program (see FIG. 18). Such a case obtains the new effects that the radiation irradiation start can be detected earlier than in the above exemplary embodiment, and processing can be simplified.

In the above exemplary embodiment, it is described that image data for offset correction and image data for fixed noise reduction correction are acquired, as the image data for use in the radiation determination function, at the same time by obtaining combined data of one lines worth of image data of the signal lines 36. However exemplary embodiments are not limited thereto, and for example an embodiment may be configured in which only a portion of the above image data is acquired in order to realize faster processing. Note that in such cases, for each of the correction normal line image data and the correction detection line image data, image data for performing offset correction and image data for performing fixed noise reduction correction may be acquired separately by the correction data acquisition processing routine program, and the offset correction and the fixed noise reduction correction may be performed separately using these data.

Explanation has been given in the above exemplary embodiment in which the radiation detection pixels 32A are configured by the thin-film transistors 10 having source and drain terminals being shorted; however, exemplary embodiments are not limited thereto. For example, the radiation detection pixels 32A may be configured such that the connection portion between the respective capacitors 9 and the thin-film transistors 10 is directly connected to the dedicated signal line for radiation detection.

There is also no requirement to utilize the pixels of the radiation detector as a sensor for radiation detection. For example, a sensor for radiation detection that generates electrical charges when radiation is irradiated may be provided at a predetermined position, such as between each pixel line or at peripheral edge portions of the radiation detector 20. Determination is then made as to whether or not radiation has been detected at the electronic cassette based on the ratio of the values (second values) obtained using the sensor and the values (first values) obtained by the radiographic imaging pixels 32B. In such cases, depending on factors such as the conversion characteristics of radiation to electrical charge of the sensor and the number of the radiographic imaging pixels 32B utilized, the magnitude relationship between the first values and the second values may be the reverse of that in the above exemplary embodiment. However, the above exemplary embodiment may still be applied to such cases.

Explanation has been given in the above exemplary embodiment of a case in which, image data that is obtained with all the thin-film transistors 10 in the OFF state is employed in the radiation determination function; however, exemplary embodiments are not limited thereto. For example, the radiation determination function may employ image data that is obtained with a specific number of the thin-film transistors 10 in an ON state, where the upper limit of the specific number being less than the number of the radiation detection pixels 32A connected to a single signal line 36B.

Explanation has been given in the above exemplary embodiment of a case in which the ratio R is calculated by Equation (3); however, exemplary embodiments are not limited thereto. For example, a ratio obtained by a computation equation in which the top and bottom of Equation (3) are interchanged may be utilized. In this case, it is determined that radiation has been detected at the electronic cassette if the ratio is smaller than the predetermined threshold value.

Moreover, explanation has been given in the above exemplary embodiment of a case in which the first value S1 and the second value S2 are acquired by summation of plural sets of image data successively obtained; however, exemplary embodiments are not limited thereto. An embodiment may be configured in which such summation is not performed, and the first value S1 and the second value S2 are acquired from only a single set of image data.

Moreover, explanation has been given in the above exemplary embodiment of a case in which the sensor portions 13 are formed from an organic photoelectric conversion material that generates electrical charge on receipt of light generated by the scintillator 8. However, exemplary embodiments are not limited thereto, and the sensor portions 13 may be formed without containing an organic photoelectric conversion material.

Explanation has been given in the above exemplary embodiment of a case in which the case 42 for housing the cassette controller 58 and the power supply section 70 inside the housing 41 of the electronic cassette 40 is disposed so as not to overlap with the radiation detector 20; however, exemplary embodiments are not limited thereto. For example, the cassette controller 58 and/or the power supply section 70 may be disposed so as to overlap with the radiation detector 20.

Explanation has been given in the above exemplary embodiment of a case in which communication between the electronic cassette 40 and the console 110 and between the radiation generator 120 and the console 110 is performed by wireless communication. However the exemplary embodiments are not limited thereto and, for example, communication between one or both of these pairs may be performed by wired communication.

While explanation has been given in the above exemplary embodiment of an example in which X-rays are applied as the radiation, exemplary embodiments are not limited thereto. Other types of radiation, such as gamma radiation may be used.

In addition, the configuration of the RIS 100 (FIG. 1), the configuration of the radiographic imaging room (see FIG. 2), the configuration of the electronic cassette 40 (see FIG. 3 to FIG. 8) and the configuration of the imaging system 104 (see FIG. 9) explained in the above exemplary embodiment are merely examples. Obviously parts not required may be omitted, additional parts may be added and connection states may be changed within a scope not departing from the spirit of the present invention.

Moreover, the flow of processing in each of the programs explained in the above exemplary embodiment (see FIG. 16 and FIG. 18 to FIG. 20) are merely examples. Obviously steps not required may be omitted, new steps may be added, and the processing sequence may be switched around within a scope not departing from the spirit of the present invention.

What is claimed is:

1. A radiographic image capture device comprising:
a radiation detector including a first sensor for radiographic image capture and a second sensor for radiation detection that is capable of directly reading out signals, the first sensor and the second sensor being integrally formed in the radiation detector; and
a determination section that determines whether or not radiation has been detected by the radiation detector based on a ratio of a first value obtained by the first sensor to a second value obtained by the second sensor,
wherein the first sensor includes a plurality of radiographic imaging pixels that each include a conversion portion that converts irradiated radiation into electrical charge and a switching element that is switched ON when reading electrical charge obtained by the conversion portion,
wherein the second sensor includes a plurality of radiation detection pixels that each include a conversion portion and are enabled for direct reading of electrical charge obtained by the conversion portions, and
wherein the switching element of each of the radiation detection pixels is shorted across switch terminals.

2. The radiographic image capture device of claim 1, wherein the first sensor includes a plurality of radiographic imaging pixels, and the second sensor is disposed between the plurality of radiographic imaging pixels or at a predetermined position in the radiographic image capture device.

3. The radiographic image capture device of claim 1, wherein at least one of the first value or the second value is a summed value of values representing electrical charge that is read a predetermined number of times from the corresponding first or second sensor.

4. The radiographic image capture device of claim 1, wherein:
the radiation detector comprises the plurality of radiographic imaging pixels and the plurality of radiation detection pixels arrayed in a matrix formation, in which an array containing only the radiographic imaging pixels and an array including at least one radiation detection pixel are included, and a plurality of signal lines, each of which is connected to the pixels arrayed in a different one of the arrays; and
the determination section uses a value representing electrical charge read from a first signal line, which is a signal line provided for the array containing only the radiographic imaging pixels, as the first value, uses a value representing electrical charge read from a second signal line, which is a signal line provided for the array including the at least one radiation detection pixel, as the second value, and determines that radiation has been detected by the radiation detection pixels if a condition of the ratio of the second value to the first value being a first threshold value or greater is satisfied, and otherwise determines that radiation has not been detected, electrical charge being read from the first signal line and the second line after switching all of the switching elements OFF.

5. The radiographic image capture device of claim 4, further comprising an offset correction section that performs offset correction on the first value and the second value to reduce the influence of electrical charge that arises from dark current occurring in the conversion portions and/or reduce the influence of switching noise that occurs when the switching elements are switched, wherein the determination section performs the determination employing the first value and the second value that have been subjected to the offset correction by the offset correction section.

6. The radiographic image capture device of claim 4, further comprising a fixed noise correction section that performs fixed noise reduction correction on the first value and the second value to reduce the influence of fixed noise that inherently occurs according to array positions of the radiographic imaging pixels and the radiation detection pixels,
wherein the determination section performs the determination using the first value and the second value that have been subjected to the fixed noise reduction correction by the fixed noise correction section.

7. The radiographic image capture device of claim 4, wherein the determination section performs the determination using, as the first value, a summed value of values representing electrical charge that is read a predetermined number of times from the first signal line and using, as the second value, a summed value of values representing electrical charge that is read the predetermined number of times from the second signal line.

8. The radiographic image capture device of claim 7, wherein the values subject to the summation are values within a predetermined range.

9. The radiographic image capture device of claim 4, wherein the determination section performs the determination a plurality of times using different combinations of the first value and the second value, and determines that radiation has been detected by the radiation detection pixels if a number of combinations satisfying the condition equals a second threshold value or greater, and otherwise determines that radiation has not been detected.

10. The radiographic image capture device of claim 4, wherein the determination section performs the determination employing the first value and the second value representing electrical charge that has been read from the first signal line and the second signal line and the first signal line and the second signal line are adjacent to each other.

11. The radiographic image capture device of claim 4, further comprising a controller that activates operation of the radiographic image capture device to capture a radiographic image with the radiation detector if the determination section has determined that the radiation detection pixels have detected radiation.

12. A radiographic image capture method comprising:
computing, for a radiation detector including a first sensor for radiographic image capture and a second sensor for radiation detection that is capable of directly reading out signals, wherein the first sensor and the second sensor being integrally formed in the radiation detector, a ratio of a first value obtained by the first sensor to a second value obtained by the second sensor; and
determining whether or not radiation has been detected by the radiation detector based on the computed ratio,
wherein the first sensor includes a plurality of radiographic imaging pixels that each include a conversion portion that converts irradiated radiation into electrical charge and a switching element that is switched ON when reading electrical charge obtained by the conversion portion,
wherein the second sensor includes a plurality of radiation detection pixels that each include a conversion portion and are enabled for direct reading of electrical charge obtained by the conversion portions, and
wherein the switching element of each of the radiation detection pixels is shorted across switch terminals.

13. The radiographic image capture method of claim 12, wherein the first sensor includes a plurality of radiographic imaging pixels, and the second sensor is disposed between the plurality of radiographic imaging pixels or at a predetermined position in the radiographic image capture device.

14. The radiographic image capture method of claim 12, wherein at least one of the first value or the second value is a summed value of values representing electrical charge that is read a predetermined number of times from the corresponding first or second sensor.

15. A non-transitory storage medium stored with a program that causes a computer to execute radiographic image capture processing, the radiographic image capture processing comprising:
computing, for a radiation detector including a first sensor for radiographic image capture and a second sensor for radiation detection that is capable of directly reading out signals, wherein the first sensor and the second sensor being integrally formed in the radiation detector, a ratio of a first value obtained by the first sensor to a second value obtained by the second sensor; and
determining whether or not radiation has been detected based on the computed ratio,
wherein the first sensor includes a plurality of radiographic imaging pixels that each include a conversion portion that converts irradiated radiation into electrical charge and a switching element that is switched ON when reading electrical charge obtained by the conversion portion,
wherein the second sensor includes a plurality of radiation detection pixels that each include a conversion portion and are enabled for direct reading of electrical charge obtained by the conversion portions, and
wherein the switching element of each of the radiation detection pixels is shorted across switch terminals.

16. The non-transitory storage medium of claim 15, wherein the first sensor includes a plurality of radiographic imaging pixels, and the second sensor is disposed between the plurality of radiographic imaging pixels or at a predetermined position in the radiographic image capture device.

17. The non-transitory storage medium of claim 15, wherein at least one of the first value or the second value is a summed value of values representing electrical charge that is read a predetermined number of times from the corresponding first or second sensor.

18. The non-transitory storage medium of claim 17, wherein:
the radiation detector comprises the plurality of radiographic imaging pixels and the plurality of radiation detection pixels arrayed in a matrix formation, in which an array containing only the radiographic imaging pixels and an array including at least one radiation detection pixel are included, and a plurality of signal lines, each of which is connected to the pixels arrayed in a different one of the arrays; and
the determining comprises, after switching all of the switching elements OFF, using a value representing electrical charge read from a first signal line, which is a signal line provided for the array containing only the radiographic imaging pixels, as the first value, using a value representing electrical charge read from a second signal line, which is a signal line provided for the array including the at least one radiation detection pixel, as the second value, and determining that radiation has been detected by the radiation detection pixels if a condition of the ratio of the second value to the first value being a first threshold value or greater is satisfied, and otherwise determining that radiation has not been detected.

* * * * *